(12) United States Patent
Dover et al.

(10) Patent No.: US 7,837,675 B2
(45) Date of Patent: Nov. 23, 2010

(54) METHOD AND DEVICE FOR SKIN TREATMENT WITH REPLACEABLE PHOTOSENSITIVE WINDOW

(75) Inventors: Jeffrey S. Dover, Newton, MA (US); Victor Lazarev, Burlington, MA (US); Daniel Lawrence Roth, Boston, MA (US)

(73) Assignee: Shaser, Inc., Woburn, MA (US)

( * ) Notice: Subject to any disclaimer, the term of this patent is extended or adjusted under 35 U.S.C. 154(b) by 1101 days.

(21) Appl. No.: 11/141,370

(22) Filed: May 31, 2005

(65) Prior Publication Data

US 2006/0020260 A1    Jan. 26, 2006

Related U.S. Application Data

(60) Provisional application No. 60/590,272, filed on Jul. 22, 2004.

(51) Int. Cl.
*A61B 18/18* (2006.01)
(52) U.S. Cl. .............. 606/9; 606/2; 607/88; 607/89
(58) Field of Classification Search .......... 607/88–94; 606/2–19; 128/898
See application file for complete search history.

(56) References Cited

U.S. PATENT DOCUMENTS

| | | | |
|---|---|---|---|
| 3,538,919 A | 11/1970 | Meyer | |
| 3,590,371 A * | 6/1971 | Shaw, Jr. | ............. 324/505 |
| 3,693,623 A | 9/1972 | Harte et al. | |
| 3,834,391 A | 9/1974 | Block | |
| 3,900,034 A | 8/1975 | Katz et al. | |
| 4,174,713 A | 11/1979 | Mehl | |
| 4,174,714 A | 11/1979 | Mehl | |
| 4,232,678 A | 11/1980 | Skovajsa | |
| 4,388,924 A | 6/1983 | Weissman et al. | |
| 4,461,294 A | 7/1984 | Baron | |
| 4,566,454 A | 1/1986 | Mehl et al. | |
| 4,608,978 A | 9/1986 | Rohr | |
| 4,617,926 A | 10/1986 | Sutton | |
| 4,819,669 A | 4/1989 | Politzer | |
| 4,905,690 A * | 3/1990 | Ohshiro et al. | ............. 607/89 |

(Continued)

FOREIGN PATENT DOCUMENTS

EP    0 913 127    5/1999

(Continued)

OTHER PUBLICATIONS

Tunnell et al., "Optimum Pulse Duration and Radiant Exposure for Vascular Laser Therapy of Dark Port-wine Skin: a Theoretical Study," Applied Optics vol. 42, No. 7 (Mar. 1, 2003), 1367-1378.

(Continued)

*Primary Examiner*—Henry M Johnson, III
*Assistant Examiner*—Lynsey Crandall
(74) *Attorney, Agent, or Firm*—Greenberg Traurig LLP; Chinh H. Pham

(57) ABSTRACT

A method for the treatment of skin including the steps of determining the skin depth for energy absorption necessary for treatment; and generating a spot size for energy impinging on the skin to provide a desired amount of energy to the desired depth for treatment. In one embodiment the selected spot size has a small diameter. In another embodiment the spot diameter is narrower than the spacing between adjacent hairs on the skin. In another aspect the invention relates to an apparatus for the treatment of skin including a source of energy; and a means for selecting a spot size for energy from the source impinging on the skin to provide a desired amount of energy to a desired depth for treatment. In another embodiment the apparatus includes an interlock to prevent the laser from producing light unless the source is positioned to irradiate only the skin.

7 Claims, 13 Drawing Sheets

U.S. PATENT DOCUMENTS

| | | | |
|---|---|---|---|
| 4,976,709 A | 12/1990 | Sand | |
| 5,000,752 A | 3/1991 | Hoskin et al. | |
| 5,057,104 A | 10/1991 | Chess | |
| 5,059,192 A | 10/1991 | Zaias | |
| 5,182,857 A | 2/1993 | Simon | |
| 5,217,455 A | 6/1993 | Tan | |
| 5,226,907 A | 7/1993 | Tankovich | |
| 5,282,797 A | 2/1994 | Chess | |
| 5,312,395 A | 5/1994 | Tan et al. | |
| 5,344,418 A | 9/1994 | Ghaffari | |
| 5,411,502 A | 5/1995 | Zair | |
| 5,425,728 A | 6/1995 | Tankovich | |
| 5,474,549 A | 12/1995 | Ortiz et al. | |
| 5,484,432 A | 1/1996 | Sand | |
| 5,486,172 A | 1/1996 | Chess | |
| 5,546,214 A | 8/1996 | Black et al. | |
| 5,595,568 A | 1/1997 | Anderson et al. | |
| 5,628,744 A | 5/1997 | Coleman et al. | |
| 5,630,811 A | 5/1997 | Miller | |
| 5,632,741 A | 5/1997 | Zavislan et al. | |
| 5,647,866 A | 7/1997 | Zaias et al. | |
| 5,683,380 A | 11/1997 | Eckhouse et al. | |
| 5,735,844 A | 4/1998 | Anderson et al. | |
| 5,752,948 A | 5/1998 | Tankovich et al. | |
| 5,752,949 A | 5/1998 | Tankovich et al. | |
| 5,766,214 A | 6/1998 | Mehl et al. | |
| 5,810,801 A | 9/1998 | Anderson et al. | |
| 5,817,089 A | 10/1998 | Tankovich et al. | |
| 5,820,625 A | 10/1998 | Izawa et al. | |
| 5,824,023 A | 10/1998 | Anderson | |
| 5,836,938 A | 11/1998 | Slatkine | |
| 5,836,999 A | 11/1998 | Eckhouse et al. | |
| 5,846,252 A | 12/1998 | Mehl, Sr. | |
| 5,853,407 A | 12/1998 | Miller | |
| 5,871,479 A | 2/1999 | Furumoto et al. | |
| 5,871,480 A | 2/1999 | Tankovich | |
| 5,879,346 A | 3/1999 | Waldman et al. | |
| 5,885,273 A | 3/1999 | Eckhouse et al. | |
| 5,916,211 A | 6/1999 | Quon et al. | |
| 5,925,035 A | 7/1999 | Tankovich | |
| 5,989,267 A | 11/1999 | Anderson et al. | |
| 6,015,404 A | 1/2000 | Altshuler et al. | |
| 6,027,495 A | 2/2000 | Miller | |
| 6,030,378 A | 2/2000 | Stewart | |
| 6,036,684 A | 3/2000 | Tankovich et al. | |
| 6,045,548 A | 4/2000 | Furumoto et al. | |
| 6,050,990 A | 4/2000 | Tankovich et al. | |
| 6,063,074 A | 5/2000 | Tankovich | |
| 6,063,076 A | 5/2000 | Mehl, Sr. et al. | |
| 6,077,294 A | 6/2000 | Cho et al. | |
| 6,080,146 A | 6/2000 | Altshuler et al. | |
| 6,080,147 A | 6/2000 | Tobinick | |
| 6,090,101 A | 7/2000 | Quon et al. | |
| 6,096,029 A | 8/2000 | O'Donnel, Jr. | |
| 6,120,497 A | 9/2000 | Anderson et al. | |
| 6,143,287 A | 11/2000 | Ben-Hur et al. | |
| 6,149,644 A | 11/2000 | Xie | |
| 6,149,645 A | 11/2000 | Tobinick | |
| 6,152,917 A | 11/2000 | Tankovich | |
| 6,165,171 A | 12/2000 | Tobinick | |
| 6,168,589 B1 | 1/2001 | Tobinick | |
| 6,168,590 B1 | 1/2001 | Neev | |
| 6,197,020 B1 | 3/2001 | O'Donnell, Jr. | |
| 6,210,402 B1 | 4/2001 | Olsen et al. | |
| 6,214,034 B1 | 4/2001 | Azar | |
| 6,217,572 B1 | 4/2001 | Tobinick | |
| 6,228,075 B1 | 5/2001 | Furumoto | |
| 6,228,078 B1 | 5/2001 | Eggers et al. | |
| 6,235,015 B1 | 5/2001 | Mead, III et al. | |
| 6,248,102 B1 | 6/2001 | Stewart | |
| 6,267,755 B1 | 7/2001 | Clementi et al. | |
| 6,267,771 B1 | 7/2001 | Tankovich et al. | |
| 6,273,883 B1 | 8/2001 | Furumoto | |
| 6,273,884 B1 | 8/2001 | Altshuler et al. | |
| 6,277,111 B1 | 8/2001 | Clement et al. | |
| 6,280,438 B1 | 8/2001 | Echhouse et al. | |
| 6,283,956 B1 | 9/2001 | McDaniel | |
| 6,287,549 B1 | 9/2001 | Sumian et al. | |
| 6,358,242 B1 | 3/2002 | Cecchetti | |
| 6,365,145 B1 | 4/2002 | Ben-Hur et al. | |
| 6,383,176 B1 | 5/2002 | Connors et al. | |
| 6,387,089 B1 | 5/2002 | Kreindel et al. | |
| 6,406,474 B1 * | 6/2002 | Neuberger et al. | 606/9 |
| 6,419,672 B1 | 7/2002 | Utsugi | |
| 6,436,094 B1 | 8/2002 | Reuter | |
| 6,485,484 B1 | 11/2002 | Connors et al. | |
| 6,508,813 B1 | 1/2003 | Altshuler | |
| 6,511,475 B1 | 1/2003 | Altshuler et al. | |
| 6,514,242 B1 | 2/2003 | Vasily et al. | |
| 6,514,243 B1 | 2/2003 | Eckhouse et al. | |
| 6,533,774 B1 | 3/2003 | Ota | |
| 6,533,775 B1 | 3/2003 | Rizoiu | |
| 6,533,776 B2 * | 3/2003 | Asah et al. | 606/9 |
| 6,544,255 B2 | 4/2003 | Stewart | |
| 6,547,781 B1 | 4/2003 | Furumoto | |
| 6,569,156 B1 | 5/2003 | Tankovich et al. | |
| 6,572,637 B1 | 6/2003 | Yamazaki et al. | |
| 6,579,283 B1 | 6/2003 | Tobinick | |
| 6,595,985 B1 | 7/2003 | Tobinick | |
| 6,605,080 B1 | 8/2003 | Altshuler et al. | |
| 6,610,052 B2 | 8/2003 | Furumoto | |
| 6,632,218 B1 | 10/2003 | Furumoto et al. | |
| 6,632,219 B1 * | 10/2003 | Baranov et al. | 606/9 |
| 6,639,190 B2 * | 10/2003 | Lerner | 219/445.1 |
| 6,648,904 B2 | 11/2003 | Altshuler et al. | |
| 6,653,618 B2 | 11/2003 | Zenzie et al. | |
| 6,659,999 B1 | 12/2003 | Anderson et al. | |
| 6,666,856 B2 | 12/2003 | Conners et al. | |
| 6,695,835 B2 | 2/2004 | Furuno et al. | |
| 6,702,808 B1 | 3/2004 | Kreindel | |
| 6,736,807 B2 | 5/2004 | Yamazaki et al. | |
| 6,749,624 B2 | 6/2004 | Knowlton | |
| 6,758,845 B1 | 7/2004 | Weckwerth et al. | |
| 6,824,542 B2 | 11/2004 | Jay | 606/9 |
| 6,824,546 B1 | 11/2004 | Yiu | |
| 7,028,634 B1 * | 4/2006 | Lee | 116/207 |
| 2001/0029364 A1 | 10/2001 | Almeida | 606/9 |
| 2002/0005475 A1 | 1/2002 | Zenzie | |
| 2002/0035360 A1 * | 3/2002 | Connors et al. | 606/9 |
| 2002/0091377 A1 | 7/2002 | Anderson et al. | |
| 2002/0097587 A1 | 7/2002 | Krietzman et al. | |
| 2002/0169442 A1 * | 11/2002 | Neev | 606/9 |
| 2003/0004499 A1 | 1/2003 | McDaniel | |
| 2004/0034319 A1 | 2/2004 | Anderson et al. | |
| 2004/0093042 A1 | 5/2004 | Altshuler et al. | 607/88 |
| 2004/0133251 A1 | 7/2004 | Altshuler et al. | |
| 2004/0147984 A1 | 7/2004 | Altshuler et al. | |
| 2004/0167501 A1 | 8/2004 | Island et al. | |
| 2004/0176754 A1 | 9/2004 | Island et al. | |
| 2004/0225339 A1 | 11/2004 | Yaroslavsky et al. | |
| 2004/0230258 A1 | 11/2004 | Altshuler et al. | |
| 2005/0063199 A1 * | 3/2005 | Levy et al. | 362/565 |

FOREIGN PATENT DOCUMENTS

| | | |
|---|---|---|
| WO | WO 86/02783 | 5/1986 |
| WO | WO 92/19165 | 11/1992 |
| WO | WO 95/03089 | 2/1995 |
| WO | WO 95/15725 | 6/1995 |
| WO | WO 98/51235 | 11/1998 |
| WO | WO 02/089688 | 11/2002 |
| WO | WO 02/094116 | 11/2002 |
| WO | WO 03/049633 | 6/2003 |
| WO | WO 03/077783 | 9/2003 |

WO WO 2004/073537 9/2004

OTHER PUBLICATIONS

Boulnois, "Photophysical Processes in Recent Medical Laser Developments: a Review," Laser in Medical Science vol. 1, 1986.

Goldman et al., "Pathology of the Effect of the Laser Beam on the Skin," Nature, vol. 197 (Mar. 2, 1963), 912-914.

Goldman et al., "Radiation from a Q-Switched Ruby Laser," The Journal of Investigative Dermatology, vol. 44 (Jan. 1965), 69-71.

Goldman et al., "Preliminary Investigation of Fat Embolization from Pulsed Ruby Laser Impacts of Bone," Nature, vol. 221 (Jan. 25, 1969), 361-363.

Goldman et al., "Replica Microscopy and Scanning Electron Microscopy of Laser Impacts on the Skin," The Journal of investigative Dermatology, vol. 52, No. 1 (1969), 18-24.

Anderson et al., "Selective Photothermolysis: Precise Microsurgery by Selective Absorption of Pulsed Radiation," Science, vol. 220, No. 4596 (Apr. 29, 1983), 524-527.

Bartley et al., "An experimental Study to compare Methods of Eyelash Ablation," Ophithalmology, vol. 94, No. 10 (Oct. 1987), 1286-1289.

Kuriloff et al., "Pharyngoesophageal Hair Growth: The Role of Laser Epilation," Otolaryngology—Head and Neck Surgery, vol. 98, No. 4 (Apr. 1988), 342-345.

Finkelstein et al., "Epilation of Hair-bearing Urethral Grafts Using the Neodymium: YAG Surgical Laser," The Journal of Urology, vol. 146, No. 3 (Sep. 1991), 840-842.

Gossman et al., "Prospective Evaluation of the Argon Laser in the Treatment of Trichiasis," Ophthalmic Surgery, vol. 23, No. 3 (Mar. 1992), 183-187.

Gossman et al., "Experimental comparison of Laser and Cryosurgical Cilia Destruction," Ophthalmic Surgery, vol. 23, No. 3 (Mar. 1992), 179-182.

Grossman et al., "Damage to Hair Follicles by Normal-mode Ruby Laser Pulses," Journal of the American Academy of Dermatology, vol. 35, No. 6 (Dec. 1996), 889-894.

Chernoff, "Selective Photothermolysis for Hair Removal," [online, retrieved on Jul. 8, 2005]. Retrieved from the Internet:< URL: http://www.lasertraining.com/med-13.htm>.

"SLS Biophile, Ltd. [formerly Mehl/Biophile]", [online, retrieved on Jul. 22, 2005]. Retrieved from the Internet:<URL: http://www.hairfacts.com/makers/laser/mehl.html>.

* cited by examiner with the same fluence rate as from broad beam

METHOD AND DEVICE FOR SKIN TREATMENT WITH REPLACEABLE PHOTOSENSITIVE WINDOW

CROSS-REFERENCE TO RELATED APPLICATION

This application claims the benefit of and priority to U.S. provisional patent application Ser. No. 60/590,272 filed on Jul. 22, 2004, the disclosure of which is incorporated herein by reference in its entirety.

FIELD OF THE INVENTION

The invention relates generally to treating tissue and more specifically to dermatologic treatment using directed energy.

BACKGROUND OF THE INVENTION

Light has been used in a wide range of medical applications for many years. In the field of dermatology high powered lasers and intense pulsed light (IPL) systems have been used to permanently remove unwanted hair, rejuvenate skin, remove veins etc. In the field of hair removal, devices remove hair from areas of the body with large diameter pulses of laser or incoherent light called intense pulsed light. One disadvantage of the above described devices is that the power (both electrical and light output) required to deliver permanent or long lasting results are extremely high, and such devices are only suitable for use in a clinical setting with trained professionals operating the devices. A further disadvantage is that the treatments are costly, painful, time consuming and only partially effective. To improve efficacy of these treatments more and more powerful devices have been marketed in an attempt to produce long lasting results. Additionally these devices utilize large diameter output beams which are known to penetrate the skin deeply and to deliver high doses of energy to the base region of the hair follicle. These newer devices which are capable of generating the "required" power level for effective long-term hair loss using a large diameter spots are large, heavy, expensive, require sophisticated cooling and are dangerous. Current prices on the market for such devices exceed $50K and the device itself can weigh more than 100 lbs. These are not devices that can be sold to individual consumers, or be operated safely in the home by average consumers.

In addition to the production of more powerful laser devices, a trend has also emerged toward larger spot sizes. Experimental results have shown that larger spots penetrate more deeply into tissue than small ones. Thus, researchers in this area, in an effort to obtain a long-lasting and more permanent result, strive to provide the larger sizes. Until now, little research has gone into understanding the actual behavior of light as it diffuses into tissue as it relates to the spot size. As a result, the use of small spot treatments has been dismissed as not feasible in this area of dermatology.

The commonly held (though incorrect) understanding of how light diffuses into skin as a function of spot size has prevented the industry from developing effective methods for hair growth modulation for the end consumer. The belief that only large diameter laser and IPL spots can cause hair loss has lead the entire industry to develop larger, more expensive and more dangerous devices; now producing more than 2900 W of output power.

The present invention relates to methods and devices that use a model for light diffusion in skin as a function of spot size. These methods and devices use a small spot size and low power radiation to achieve short-term hair growth modulation as well as for the treatment of other skin disorders. Furthermore the present invention demonstrates a device that can be highly effective using a fraction of the power required by today's typical devices. The device disclosed herein can be mass produced for safe use in the home with excellent results.

SUMMARY OF THE INVENTION

The invention relates in one aspect to a method and apparatus for the treatment of skin. In one embodiment the method relates to scanning a small area radiation field over the skin at a predetermined rate and at a selected fluence and wavelength to heat a target chromophore to a level sufficient to cause a result. In one embodiment the result is short term hair growth rate modification.

The invention relates in another aspect to a method for the treatment of skin including the steps of determining the skin depth for energy absorption necessary for treatment and generating a spot size such that the energy impinging on the skin provides a desired amount of energy to the desired depth for treatment. In one embodiment the selected spot size has a diameter narrower than the spacing between adjacent hairs on the skin. In yet another embodiment in which the treatment is hair removal, the depth is selected to be near the location of the follicular bulge of the hair. In still yet another embodiment the method further includes the step of selecting a wavelength of light suitable for treatment.

In another aspect, the invention is a method for the treatment of a region of skin including the steps of generating a small spot size for energy impinging on the skin to provide a desired amount of energy to a desired depth for treatment of the region of skin and scanning the small spot over the region of skin to be treated.

In yet another aspect the invention relates to a method for the treatment of a region of skin including the steps of generating a small spot size for energy impinging on the skin surface to provide a desired amount of energy to a desired depth for treatment of the region of skin and scanning the small spot over the region of skin to be treated. The spot is of a size such that the area of treatment at the desired depth is much larger than the size of the spot on the skin surface.

In another aspect, the invention relates to an apparatus for the treatment of skin including a source of energy and a means for generating a small spot size for energy from the source impinging on the skin to provide a desired amount of energy to a desired depth for treatment. In one embodiment the energy source is a laser producing a desired wavelength of light for treatment. In another embodiment the energy is generated by a flash lamp, with subsequent spectral selection of the emitted light by optical filters.

Yet another aspect of the invention is a method for controlling the energy used for the treatment of a region of skin including the steps of generating a small spot size for energy impinging on the surface of the skin to provide a desired amount of energy to a desired depth for treatment of the region of skin; moving the small spot over the region of skin to be treated; measuring the rate of movement of the spot over the skin surface; and controlling the amount of energy reaching the desired depth for treatment in response to the rate of movement of the spot over the skin surface. In one embodiment the method further includes scanning the small spot over the surface of the skin at a scanning rate; wherein the step of controlling the amount of energy reaching the desired depth for treatment includes adjusting the scanning rate. In another embodiment of the method, the scanning rate is adjusted in real time. In yet another embodiment the controlling of the amount of energy reaching the desired depth for treatment includes adjusting the amount of energy in the spot impinging on the skin.

Another aspect of the invention is an apparatus for the treatment of a region of skin. The apparatus includes a source of energy which generates a small spot size for the energy impinging on the skin and a means for scanning the spot of energy over the surface of the skin. In one embodiment the means for scanning includes a device selected from the group consisting of galvanometric scanning mirrors, linear actuators, rotating optical wedges, cam driven reciprocal mirrors and rotating polygons. In another embodiment the means for generating a spot size of energy produces a treatment area at the desired depth of treatment much larger than the area of the spot at the surface of the skin. In yet another embodiment the apparatus further includes a means for measuring the rate of movement of the spot over the skin surface; and a controller in communication with the means for measuring the rate of movement of the spot over the skin surface. The controller controls the amount of energy reaching the desired depth for treatment in response to the rate of movement of the spot over the skin surface.

In another embodiment the controller is in communication with the means for scanning. The means for scanning scans the spot at a scanning rate; and the controller adjusts the scanning rate in response to the rate of movement of the spot over the skin surface in real time. In another embodiment the controller is in communication with the source of energy and adjusts the intensity of the energy reaching the skin in response to the rate of movement of the spot over the skin surface in real time. In another embodiment the apparatus further includes an indicator in communication with the means for measuring the rate of movement of the spot over the skin surface which indicates when the rate of movement of the spot over the skin surface is outside a predetermined range. One embodiment also includes a safety means for disabling the device if the device is not properly in contact with the skin surface.

BRIEF DESCRIPTION OF THE DRAWINGS

These and further advantages of the invention will be easily understood by reference to the specification and drawings in which:

FIG. 14 is still yet another embodiment of a scanning device using a rotating polygon;

FIG. 14d is a portion of the diagram of FIG. 14a;

DESCRIPTION OF THE PREFERRED EMBODIMENT

The theory of light diffusion in scattering media is used to determine the amount of fluence needed to have a cosmetic effect on the skin. In the near IR spectral region the absorption coefficient for skin is $\mu_a$=0.02 mm$^{-1}$. This coefficient gives the number of events of absorption for an average photon traveling along a 1-mm path. The reduced scattering coefficient for skin is $\mu'_s$=1.6 mm$^{-1}$. This coefficient determines the number of events of photon isotropic scattering on the same path. Thus the possibility of a photon scattering is ~2 orders of magnitude higher than for its absorption. That is why the light propagation in skin is described by diffusion equation rather than by regular wave theory.

Figure 1:
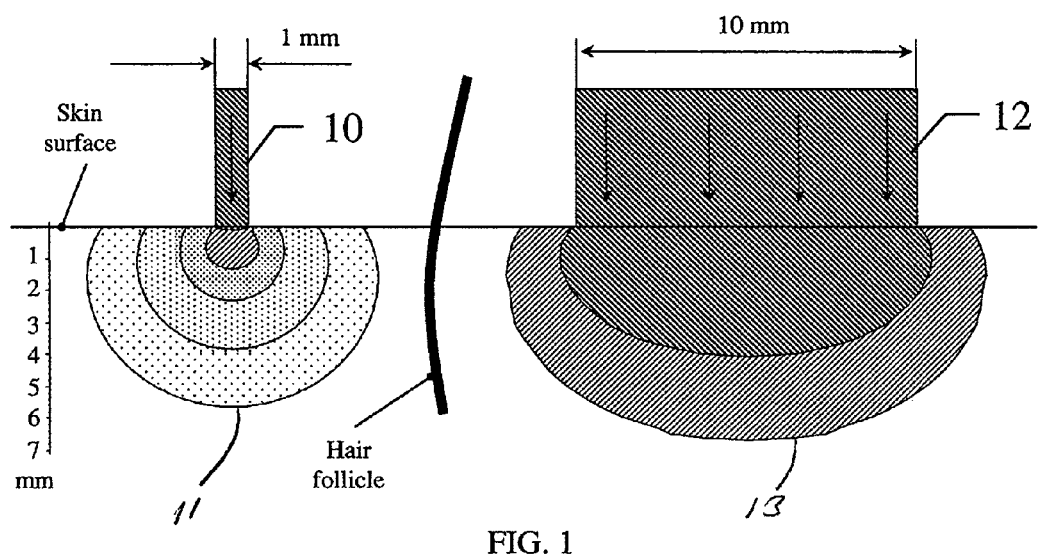
FIG. 1 is a schematic diagram of the relationship between spot size and penetration depth for illumination on human skin.
Figure 2:
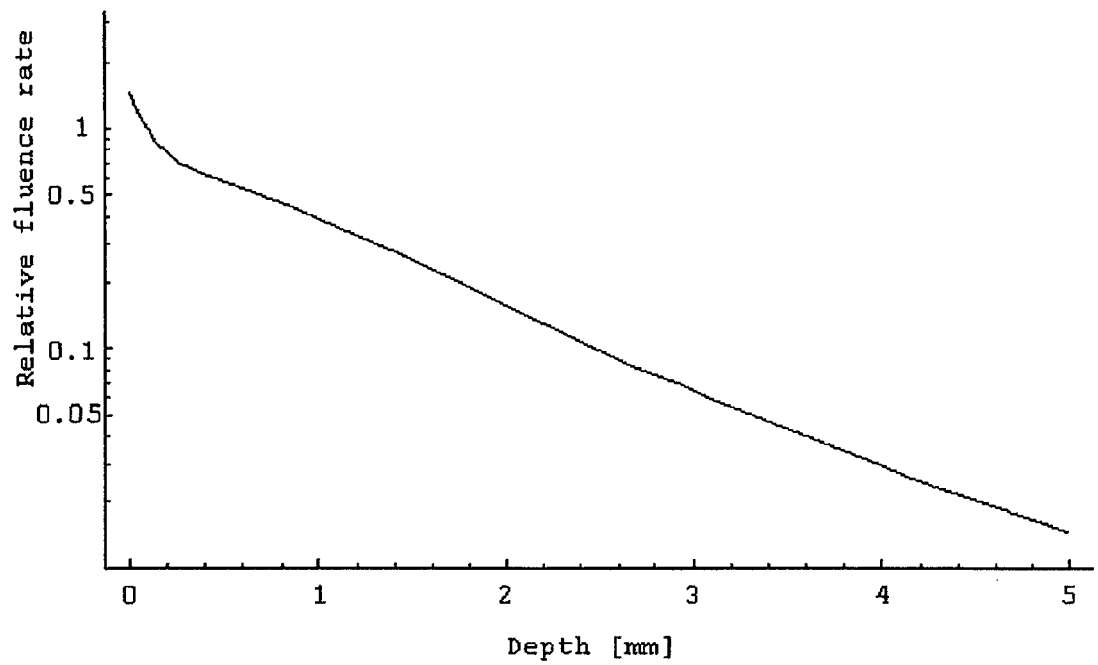
FIG. 2 shows the decrease of fluence rate with depth along the beam axis for 1-mm beam.

Referring to FIG. 1, two laser beams of equivalent power density or irradiance are seen in cross section penetrating a skin region with a hair follicle shown for scale. The first beam 10 is narrow and as a result its power will diffuse into the skin near to the surface forming a pattern roughly as outlined. The drawn contours 11 correspond to the fluence rate levels (W/cm$^2$) of 1.0, 0.3, 0.1, 0.03, and 0.001 times the surface radiance. The contours 13 of the larger beam 12 correspond to fluence rate levels of 1.0 and 0.3 times the surface radiance. The larger beam 12 clearly shows that at predetermined depth it is able to deliver power close to the original power, while the narrow beam 10 shows that at the same predetermined depth its delivered power is a fraction of its original power. Generally to achieve a cosmetic result, such as a short-term hair growth, the predetermined depth is 1-6 mm below the surface and the delivered fluence at 1-6 mm below the surface is 0.1-10 J/cm$^2$. FIG. 2 shows the rapid decrease of fluence with depth along the beam axis of a one mm beam.

But if the total power of both beams that is required to provide the same fluence at the desired depth is considered, the advantage of narrow beam will be seen. As known from light diffusion theory, the fluence $\Phi_1$ far from the surface is described by the equation:

$$\Phi_1 = \frac{3\mu'_s}{4\pi} P_1 \frac{\text{Exp}\left[-\sqrt{3\mu'_s\mu_a}\,(z - 1/\mu'_s)\right]}{z - 1/\mu'_s} \quad (1)$$

where z is the depth and $P_1$ is the power of light source. Referring again to FIG. 2, the fluence from a one mm beam has an exponential behavior at a depth of more than one mm, therefore showing that the behavior of the beam can be described by equation (1). The surface fluence rate provided by the broad beam can be expressed as:

$$\Phi_2 = P_2/\pi R^2 \quad (2)$$

where $P_2$ is total power delivered by the beam, and R is the radius of the broad beam.

If the right parts of equations (1) and (2) are equated, how much power is required by a large beam versus a small beam to achieve the same fluence at a desired depth can be determined. The ratio of $P1/P_2$ is then given by:

$$\frac{P_1}{P_2} = \frac{4(z - 1/\mu'_s)}{3\mu'_s R^2} \text{Exp}\left[\sqrt{3\mu'_s\mu_a}\,(z - 1/\mu'_s)\right] \quad (3)$$

Figure 3:
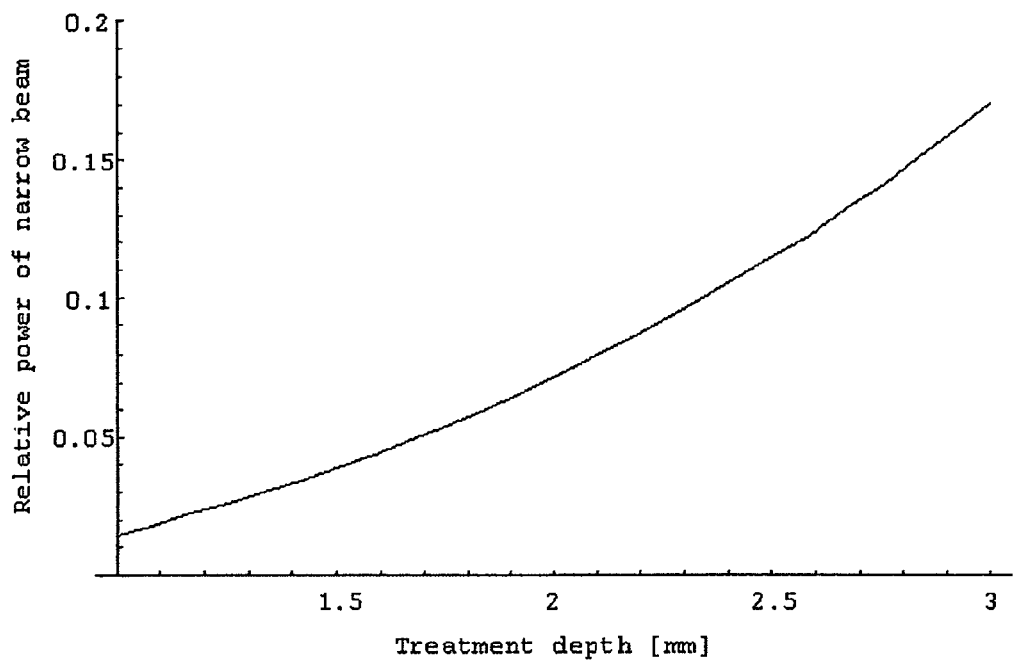
FIG. 3 is a graph of the relative power of narrow beam plotted against depth showing the relative power of a small beam compared to a wide beam having the same fluence.

Equation (3) describes the fraction of broad beam power that a narrow beam must have to deliver the same fluence to the depth z as is delivered by a large beam of radius R. FIG. 3 illustrates a plot of this equation for R=5 mm (beam diameter 10 mm), and $\mu'_s$=1.6 mm$^{-1}$, $\mu_a$=0.02 mm$^{-1}$ corresponding to human dermis.

FIG. 3 demonstrates that for all depths within the range of interest the power of narrow beam is much less than that required for 10 mm beam. The power required to deliver specific fluence to the mean depth of 3 mm is next calculated using a fluence level of 1.5 J/cm$^2$. It is determined that for a broad beam to deliver 1.5 J/cm2 to the target, the original beam should also be 1.5 J/cm$^2$ since little power is lost at the relevant depths. If the beam has a diameter of 10 mm then the total area of the beam is 78.5 mm$^2$ and the total delivered energy is 1.18 J. If the pulse duration (length of time the target is directly illuminated) is equal to 30 ms (a fairly standard pulse duration as known in the art), then the output power of the broad beam device must be 39 W. From equation (3) and FIG. 3, the same fluence will be delivered to a three mm depth by narrow beam using only 6.8 W of power. Thus the narrower beam requires that less power be developed for the same effect.

It is known in the art that laser diodes are a good way to develop laser beams for such dermatological treatments. It is also known that diode lasers have a limited power output per chip, and to develop high power so called "diode laser bars" are utilized. These laser bars are a sequence of many diode lasers which then use optics to combine the numerous output beams into a single more powerful beam. With present technology a single laser diode chip may only be able to produce up to 7 or so Watts of power. If more power is needed then the cost of producing such device will grow dramatically due to the optics needed to combine the beams; the added cost for producing a bar rather than a single chip; and the larger power supply needed to power such a system.

By discovering that certain effects such as short term hair growth modulation are actually possible at low fluences, and by determining the actual behavior of light as it diffuses in skin, the current invention discloses a method and apparatus to cause a cosmetically valuable result such as the retardation of hair growth with very low power. A device capable of employing this method could be produced very inexpensively and can also be manufactured in consumer quantities. Furthermore, because the invention describes a low fluence method only a single laser diode is needed and hence the total cost of the device is further reduced because the optics for beam shaping is simplified by using a laser diode chip that is a "point" light source. This single low power laser device also simplifies the electronics and mechanical requirements by lowering the power needed and eliminating many optical stages for collimation and shaping.

The current invention also takes advantage of a further innovation in which the small beam is moved across the skin to treat large areas. In the prior art the high power small beams were held in position over a precise target such as a single hair by an apparatus. In some cases, an actual optical fiber was introduced into the follicle to deliver the treatment beam. By moving the beam across the skin and harnessing the diffusive behavior of the light in scattering media the operator can now treat large areas rapidly.

Figure 4:
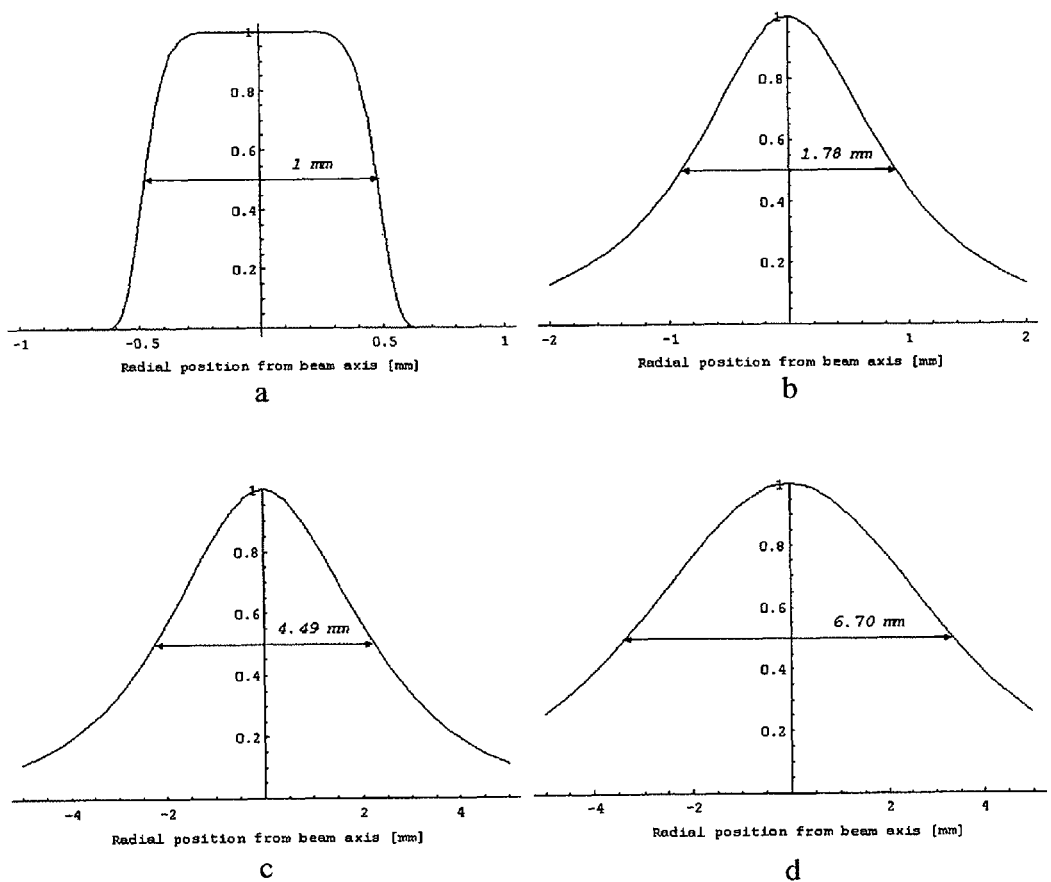
FIG. 4 (a-d) are graphs of the relative fluence generated by a one mm beam passing through skin to different depths.
Figure 5:
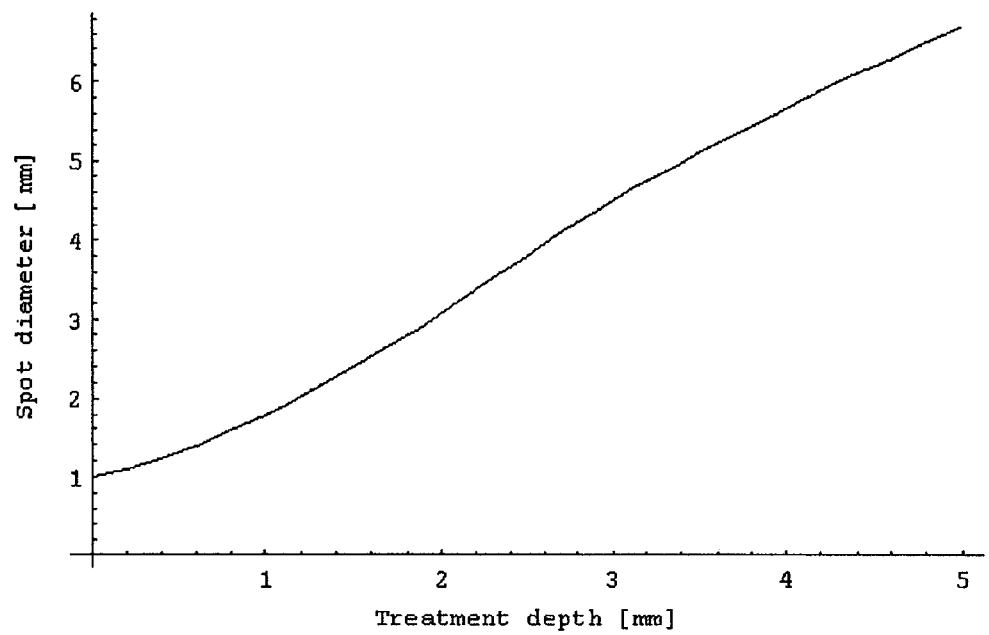
FIG. 5 is a graph showing the relationship between spot diameter and treatment depth.

Referring to FIG. 1 again, in the case of the narrow beam 10, the model shows that the actual diameter of the treatment area below the skin surface is much larger than the diameter of the original beam. This is not so in the case of the wide beam 12. This conclusion is confirmed by a calculation of the fluence distribution at different depths, which are generated by narrow beam. FIG. 4 (*a-d*) show the fluence profile produced by 1-mm beam at the depths: 0, 1, 3, 5 mm. In this figure, all curves are normalized to the axial fluence at the same depth. The absolute values of axial fluence are depicted in FIG. 2. The diameter of illuminated spot at each depth can be determined as Full Width at Half Maximum (FWHM) of the curve. FIG. 5 shows the continuous dependence of spot diameter on the depth for 1-mm beam.

Figure 6:
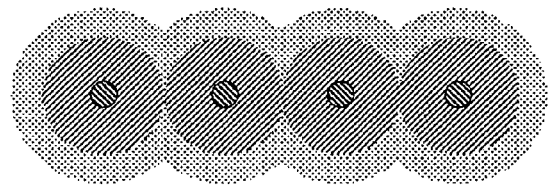
FIG. 6 is a schematic diagram of non-continuous treatment over an area of skin.

By utilizing the behavior of the beam as it penetrates the skin, the present invention is able to function in such a way as to separate the concepts of direct illumination and treatment area. In other words, the present invention utilizes the new discovery that when using a small spot, the treatment area is substantially larger than the illuminated beam diameter on the surface. Referring now to FIG. 6, a plan view of a treatment area is shown that takes advantage of the fact that a larger area is treated at the desired depth than is directly illuminated on the surface. Using a non-continuous movement across the skin surface, this fact enables treating a continuous area while only directly illuminating a fraction of the total area. Also, by using the method of continuous movement across the skin, it is possible to reduce the time needed for treatment by increasing the rate of movement and decreasing the time of direct illumination while still achieving good efficacy. It is easily understood that it is advantageous to reduce the time needed for direct illumination, while covering large areas quickly. The time between pulses may be selected to allow the skin to cool so as not to damage areas of the skin not under treatment (for example areas adjacent the hair follicle being removed).

A further aspect of the invention is the continuous movement of the beam across the surface while in CW or continuous wave mode. Prior art systems typically use Pulse Mode (PM) for treatment in which the device fires a high power pulse of light to treat an area. This has several disadvantages. One disadvantage is the non-linear behavior in power output as laser systems energize and come to equilibrium. As a result, the amount of energy delivered to the target is not constant, nor is it easily calibrated. Furthermore, in prior art systems with large diameter beams utilizing PM, the operator physically moved the device a step at a time prior to exposing the skin to a pulse of light. This is cumbersome, and also introduces the likely result of not treating areas completely due to human error of moving the device in irregular steps, unlike in the present invention in which scanning of the beam occurs which automatically.

Figure 7:
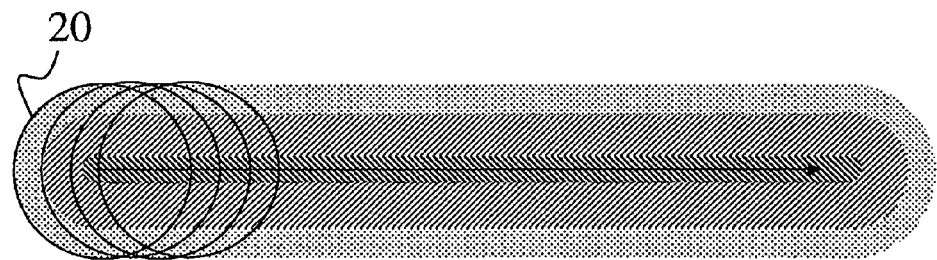
FIG. 7 is a schematic diagram of continuous treatment of an area of skin.

In the present invention, in either the CW case or the scanned PM case, the treatment time (TT) or the amount of time an area is treated, can be calculated either as the length of time the beam directly illuminates a point on the surface as it passes by, or by the amount of time the subcutaneous area is treated directly or indirectly through the diffusive properties described above. FIG. 7 shows the treatment area using a narrow beam continuous wave laser. The area that can be treated using this method is larger than the area covered by direct illumination. In FIG. 7 the series of circles shows the area which can be treated over time is different from the amount of time any area of skin spends under direct illumination. In the very first circle of treatment 20, one can easily see that some of the areas being treated have not been illuminated directly at all.

Continuous movement of the illumination spot over the surface brings one more advantage related to the pulse mode source. The treatment efficiency depends on the total fluence [J/cm$^2$] delivered by the beam to the treated area, rather than on its fluence rate [W/cm$^2$].

When treatment is provided by a stable spot from a pulsed source, the distribution of both of these parameters inside the treated medium is the same because the treatment area depends on the beam width. As an example, in this case the fluence from the laser beam of 1 mm diameter will depend on the depth as shown in FIG. 2 above.

However, if illumination is provided by a CW source and the spot is moved across the surface, the duration of treatment is determined by scanning speed and spot diameter. The last parameter grows with the depth because of light diffusion. Therefore, the treatment duration increases with depth in the same manner as the spot diameter. As fluence is the product of the fluence rate and the pulse width, it decreases slowly with the depth compared to the fluence rate.

Figure 8:
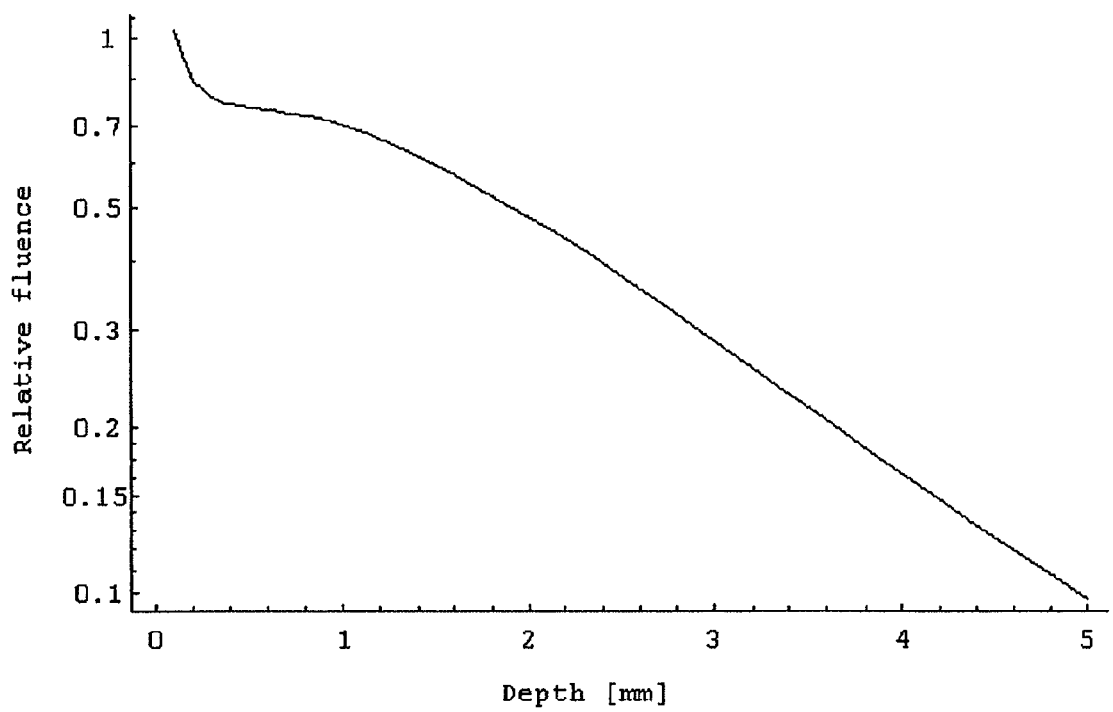
FIG. 8 is a graph depicting the dependence of fluence on depth for the surface beam diameter of 1 mm.

FIG. 8 shows the dependence of fluence on depth for the surface beam diameter of 1 mm. The curve is calculated as a product of functions shown in FIG. 2 and FIG. 5. From a comparison of FIGS. 2 and 8 it is seen that fluence is decreased by 10 times at the 5 mm depth, while fluence rate drops almost to 1% of the surface amount at the same depth. Therefore, the amount of fluence delivered to the 5-mm depth from moving CW beam is higher by almost 10 times than from the stable pulsed beam, if surface fluence is the same in both cases.

Figure 9:
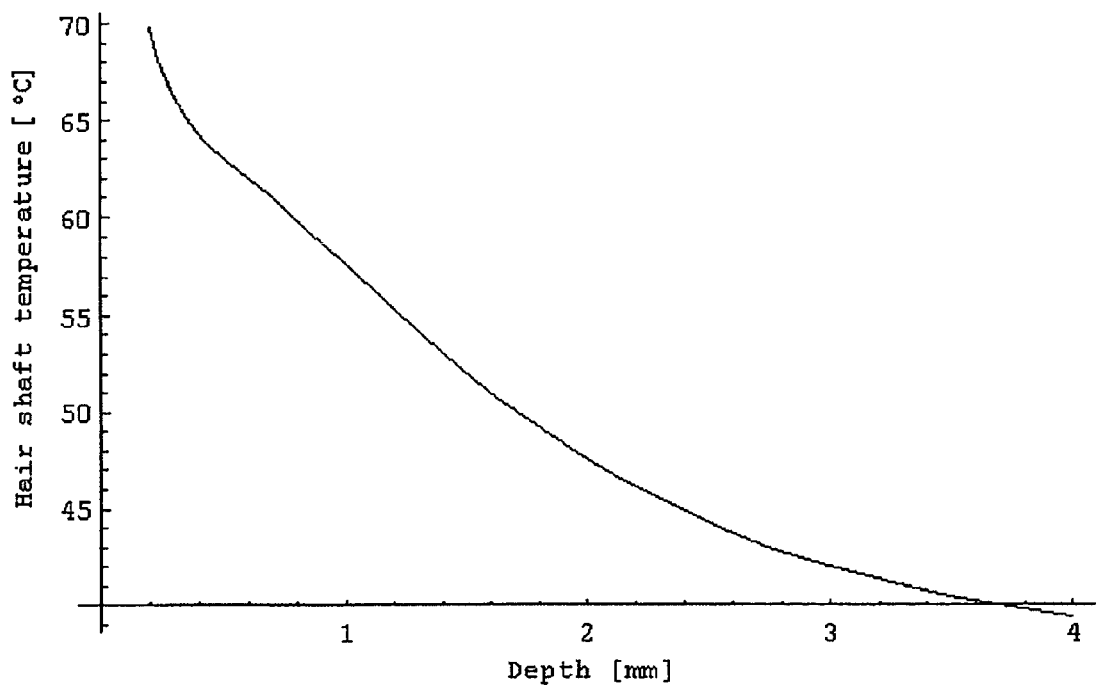
FIG. 9 is a graph depicting the distribution of the highest temperature along the dark hair shaft produced by a moving narrow beam.

A further aspect of the invention is that, unlike what is described in the prior art intense treatment of the base of the hair follicle, or the papilla, may not be needed to gain a cosmetic result. The current invention is based on the discovery that treating the upper and mid-portion of the follicle may be sufficient to cause hair growth modulation. FIG. 9 illustrates the distribution of temperature along the dark hair shaft, which is produced by 1.5 W beam with 1-mm of surface spot diameter moving with the speed of 100 mm/sec. From this graph it is seen that the upper portions of the hair are brought to a higher temperature. The temperature of portions of the hair located deeper than 3 mm is below 42° C. This keeps those portions from being severely damaged. The hair bulb is generally positioned deeper than 3 mm from the skin surface.

It should be noted that for broad beams the depth discrimination is achieved using shorter wavelengths only. This is because the penetration depth of light is strongly decreased with shortening wavelengths because of scattering and absorption. This is different with the use of a narrow beam where penetration is controlled by the geometry of illumination rather than the wavelength of light.

Figure 10:
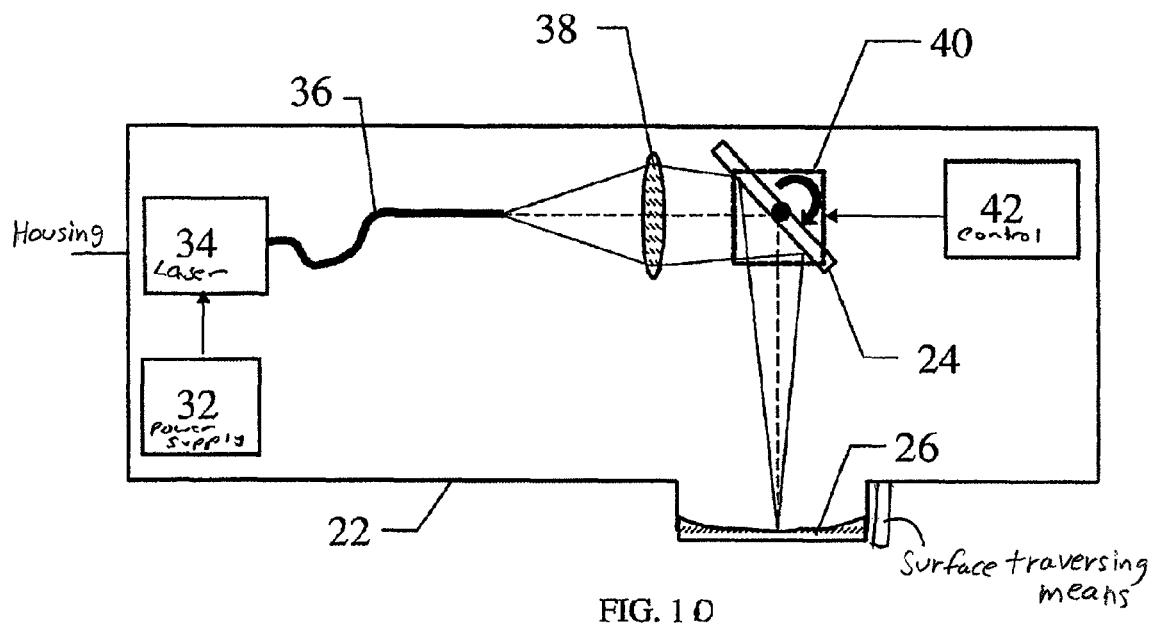
FIG. 10 is an embodiment of a treatment device constructed in accordance with the invention and using a galvanometric mirror for the scanning device.

Referring to FIG. 10, to implement this method of hair growth modulation, a hand-held optical head 22 containing a laser 34 and an optical system which distributes laser beam over a diameter of about 1 mm on the output window 26 may be used. The window 26 is placed in direct contact with skin. To provide the short treatment duration, the laser either works in continuous wave (CW) mode with simultaneous movement of the focused spot or in pulse mode (PM).

The speed of movement (V) of the spot over the treatment area for CW mode is determined by the desired amount of pulse width ($\tau$) and the diameter of treated area (D):

$$V=D/\tau \quad (4)$$

When diameter of directly illuminated spot (d) is small, the diameter of treated area is larger because of light diffusion, as shown in FIGS. 4-7. For d=1 mm, the factor of increase K is between 1 and 4 depending on treatment depth. The exact amount of factor K for any depth is shown in FIG. 5. Therefore, to provide the common pulse width ($\tau$=30 ms), the optical head should be moved with the speed:

$$V=Kd/\tau \quad (5)$$

within the range (33~133) mm/sec. The speed for other pulse widths ($\tau$) is determined by equation (5).

Figure 11:
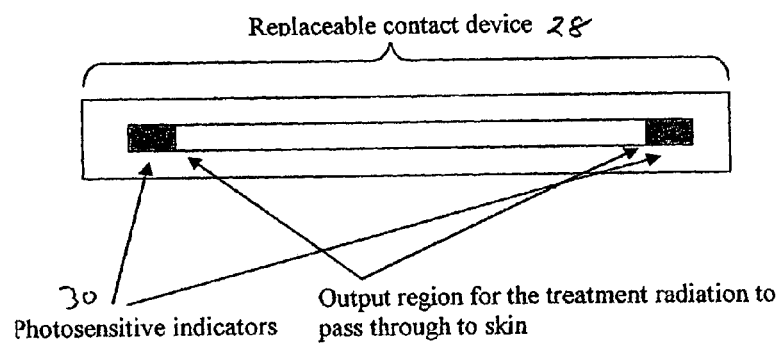
FIG. 11 is an embodiment of a contact device as constructed in accordance with the present invention.

In one embodiment of the present invention, the window 26 of the apparatus incorporates a replaceable transparent contact device 28 (FIG. 11) that is able to perform multiple functions. In one embodiment the replaceable contact device is in the form of a flat plastic (or other suitable material) covering that protects the apparatus from contaminants such as skin oils, dander, cosmetics, or other undesirable materials. Additionally since the preferred means of operation calls for the apparatus to be drawn across the skin repeatedly, the hair shafts as well as the skin itself will cause abrasions to the contact device which will impair the transmission of the treatment radiation from passing efficiently into the treatment area of the skin. The prior art systems tend to employ expensive abrasion resistant materials such as sapphire, fused silica, or other rare and exotic materials in a permanently affixed output window. For reasons of efficacy it is desirable to have the contact device remain abrasion free such that the treatment radiation is able to maintain as close to loss-less transmission into the skin as possible.

One embodiment of the invention includes a replaceable contact device that is discarded after a predetermined number of uses. This replaceable contact device is shown generally in FIG. 11. In another embodiment the replaceable contact device includes areas of material that are photosensitive 30 such that after a predetermined amount of radiation energy is absorbed by these elements, the color or visible characteristics are modified to be an indicator to the operator that the contact device should be replaced. In yet another embodiment a sensor in the apparatus monitors the amount of treatment radiation that has been transmitted through the contact device since it has been installed and causes an indicator to indicate to the operator when the replaceable contact device should be replaced to maintain proper efficacy.

In still yet another aspect of the invention the sensor is mounted in the apparatus and the replaceable contact device is configured to enable the sensor to pass through the window to make contact with the skin proximal to the treatment area. If the sensor is not mechanical, but is optical or other means not requiring contact with the skin proximal to the treatment area, the window is properly shaped to enable the correct configuration of the sensing field to be passed through into the proximity of the treatment region. In still yet another embodiment the sensor is a part of a circuit that detects if the sensor is not in close proximity to the skin and if not, turns off power to the light source. This interlock reduces the likelihood of eye damage by preventing the beam from forming if the skin is not in a position to absorb the light radiation.

In a preferable embodiment, the laser spot is linearly moved back and forth across the output window of the device by a scanning system incorporated in the optical head. The amount of scanning speed is selected in accordance to the equation (5). Movement of the device in a direction perpendicular to this periodic scanning direction is performed manually.

Figure 12:
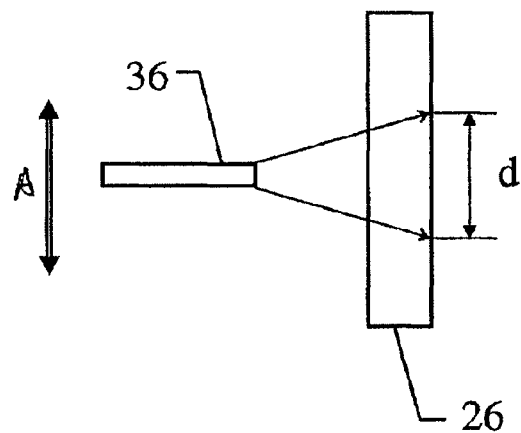
FIG. 12 is another embodiment of a scanning device using a moving optical fiber.
Figure 13:
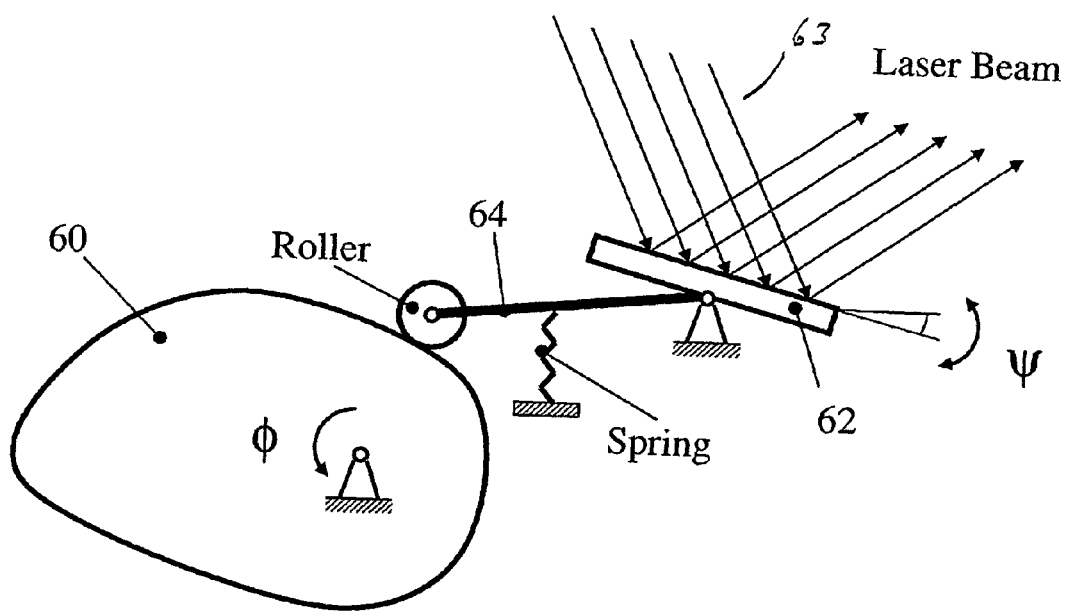
FIG. 13 is yet another embodiment of a scanning device using a cam.
Figure 12A:
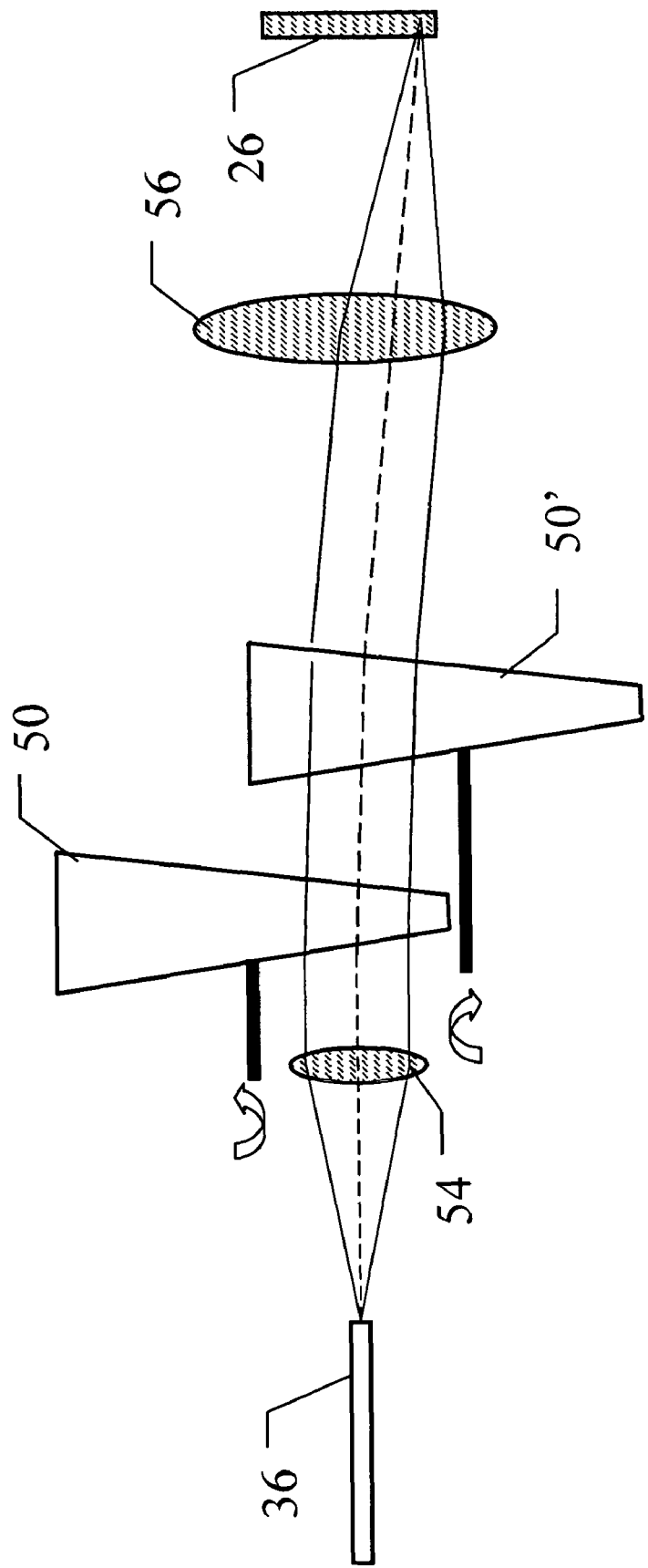
FIG. 12a is yet another embodiment of a scanning device using rotating wedges.

In general, the methods for optical beam deflection which can be utilized in the invention to provide one-dimensional scanning of the output spot can be divided generally into five classes: light reflection from periodically moved surfaces; light refraction by periodically moved transparent bodies; periodic movement of the light source; light diffraction by ultrasound waves and light refraction in crystals controlled by varying electric field. Some embodiments utilizing some of these classes of scanning systems are described below. In particular FIGS. 10, 13, and 14 are embodiments of reflective systems; FIG. 12 is an embodiment of a system involving periodic movement of the light source; while FIG. 12a is an embodiment of a refractive system.

Referring again to FIG. 10, a scanner based on an oscillating mirror controlled by a galvanometric system is shown. A power source 32 supplies current to a laser 34, which delivers the laser light to the hand-held optical head 22 by means of an optical fiber 36. Light from the fiber 36 is expanded by an optical lens system 38 to the desired diameter and projected to an output window 26 after being reflected by an oscillating mirror 24. The oscillating mirror is moved by a galvanometer 40 under the control of a control system 42. The output window 26 can be made as a cylindrical plano-concave lens to serve as a field flattener.

In one embodiment the power supply 32 draws its power from an electric outlet. In another embodiment, the handheld device 22 includes batteries. It is well known that the power requirements of today's laser output devices such as diode or solid state lasers are beyond the limits of off-the-shelf standard battery types. In one embodiment the present invention is designed for use with specially adapted, high-output batteries employing technology such as Ni Cd which are possible to develop to discharge their entire power supply in a short period of time with high output power. In one embodiment of the present invention, the apparatus is calibrated to use a fast discharge, replaceable battery component that the operator can easily remove and replace or recharge. The apparatus disclosed here also contains a monitoring means for tracking the level of power in the battery unit to ensure that enough power is available to provide a therapeutic radiation level. This monitoring means will also be configured to read information stored in the battery to ensure that it is the proper type so as to avoid powering the apparatus with an unsuitable battery that may cause damage to the device. By providing a microcontroller or other suitable logic that is able to monitor the identity and parameters of the high output battery supply the operator can be assured of proper operation and satisfactory results.

In another embodiment the battery is fitted with specifically shaped contact points and an overall shape such that only properly designed or "authorized" batteries can be fitted into the apparatus. Due to the complicated internal workings of the small field radiation device it is critical that the device only be fitted with conforming power source such that the correct amount of output radiation can be expected. It is well known that the output power of diode type laser chips, such as those disclosed for use in the apparatus of the invention, have output power in proportion to the input power. It is clear that a battery source having too high an output could cause burns in the skin region of the user.

FIG. 12 shows an embodiment of the handheld device and the scanning system with minimal optics. In this embodiment the laser light is again delivered by an optical fiber 36 whose tip is mechanically moved back and forth (arrow A) across the output window 26 by an actuator (not shown). As the light diverges from the end of the fiber, the desired spot size is formed. In one embodiment the actuator is the same as is used in computer disk drives.

FIG. 12a shows an embodiment of beam scanning provided by two similar transparent 50, 50' wedges rotating with the same speed in the opposite directions. The laser beam is collimated by lens 54 and passes sequentially through two wedges, which deflect it by a changing angle as the wedges rotate. An objective lens 56 transforms the varying incident angles into the different positions of the focused spot on the output window 26.

FIG. 13 shows another embodiment of the scanner based on a rotating cam 60; a non-round cylinder eccentrically positioned on the motor axis. The cam 60 mechanism provides the conversion of uniform motor rotation into angular reciprocation of mirror 62. The scanning of the laser beam 63 is achieved by its reflection from the oscillating mirror 62. The angular movement of rocker 64 is determined by the cam 60 profile and its rotational speed because cam 60 and rocker 64 are in permanent contact provided by roller and spring. Mirror 62 is connected to rocker 64 and has a common rotational axis. The angular mirror position depends on the rotational angle of cam 60. The working range is limited by linear part of the curve when the output angle of light reflected from the mirror is uniformly increased with angular motor position (and correspondingly, with time). After the end of each working cycle, the mirror is quickly returned to the initial position. This is necessary to provide unidirectional beam scanning. The ratio of working range angle to the full rotation angle of 360° gives the amount of duty cycle. It should be noted that it is possible to provide a scanning mechanism which permits the beam to be scanned in both directions.

FIG. 14 shows another embodiment of the scanner based on the beam reflection from the rotating polygon 70. The polygon 70 can be a prism having a mirrored surface. This is a compact design, which in addition to being compact, is free from mechanical vibrations produced by other presented embodiments. Polygon-based scanning systems are broadly used in imaging optical devices, such as laser printers. They are generally designed to solve the problem of focusing a scanning beam within extremely small spot size of a few microns. The task of the present invention is to position a spot which is about 1 mm in diameter. For this reason, the design principles of the present invention differ significantly from those usually encountered in optical imaging devices.

In more detail, the characteristics of a polygon-based embodiment may be derived from some general input parameters. Referring to FIGS. 14a-d, in each figure (NA) is the numerical aperture of fiber; (M) is the linear magnification; D is the polygon diameter; $\alpha=360°/n$ which is the angle between neighboring faces of polygon (where n is the number of faces); $\gamma$ is the angle of light incidence to the polygon face in the perpendicular plane to the rotational axis for the middle point of the scanning line; L is the scanning length; d is the output spot diameter and C is the duty cycle for the spot scanning.

Figure 14A:
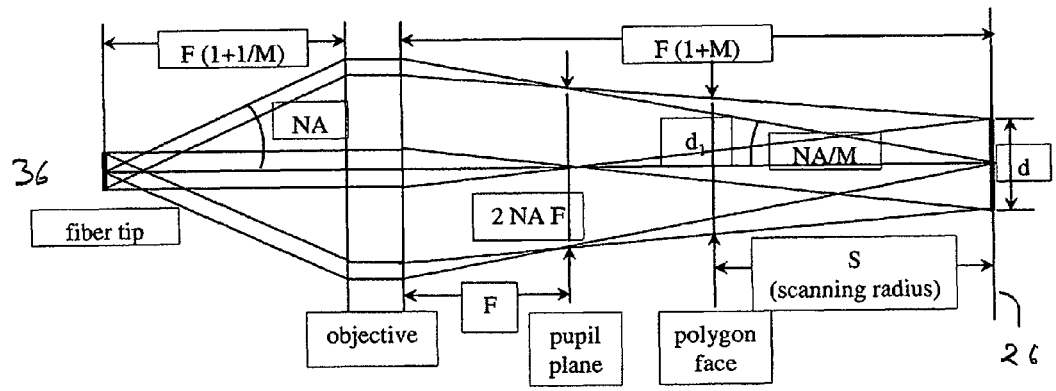
FIG. 14a is a ray diagram of a paraxial model of an embodiment of the polygon-based scanner of FIG. 14.

FIG. 14A shows the paraxial optical model of the polygon based scanner. Laser light is delivered into system by fiber 36, which tip is imaged with magnification (M) onto the plane of output window 26 within the spot diameter (d). The objective is described by two cardinal planes. The chief and marginal rays are shown for central and edge points of fiber tip. As chief rays are parallel to the optical axis, the pupil is positioned in the back focal plane of objective. ($d_1$) is the beam diameter at the polygon face.

Figure 14B:
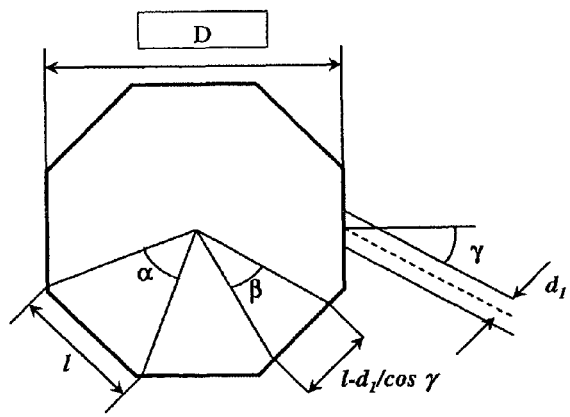
FIG. 14b is a schematic diagram of an embodiment of the polygon of FIG. 14 showing the various geometric features.

FIG. 14b shows the polygon geometry that allows derivation of the following:

The facet length is given by the equation:

$$l = D \tan(\alpha/2) \tag{6}$$

Duty cycle (C) is defined as the useful fraction of the scanning period when the laser beam is completely reflected by the polygon face without truncation by its edge:

$$C = (l - d_1/\cos\gamma)/l \tag{7}$$

The scanning angle ($\beta$) is given by:

$$\tan(\beta/2) = C \tan(\alpha/2) \tag{8}$$

The beam diameter ($d_1$) at the polygon face is derived from equations 6 and 7:

$$d_1 = D \cos\gamma (1-C) \tan(\alpha/2) \tag{9}$$

Figure 14C:
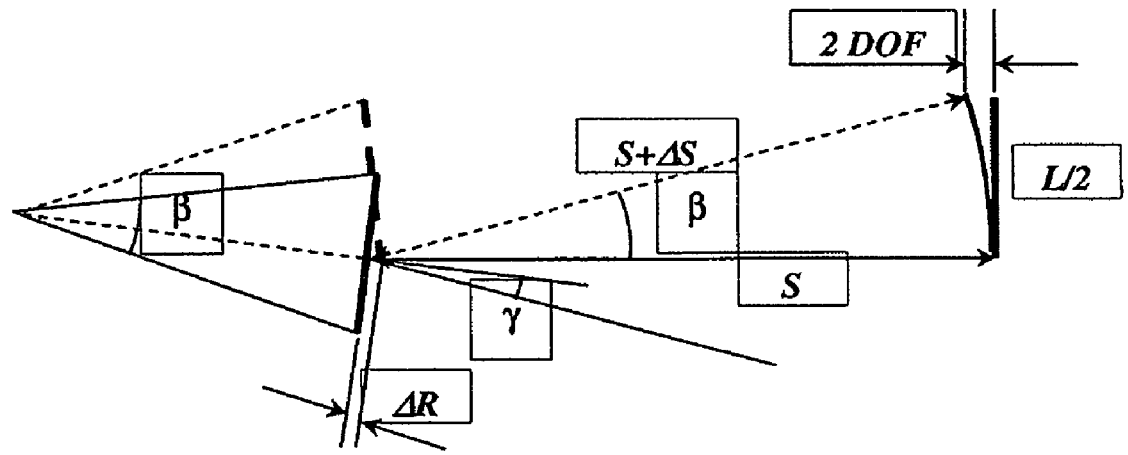
FIG. 14c is a schematic diagram of the scanning geometry of an embodiment of the polygon of FIG. 14.

Referring also to FIG. 14c, additional parameters can be derived, such as the scanning radius (S), which is given by:

$$S = L/(2 \tan\beta) \tag{10}$$

As polygon is not round, the distance between polygon and image surface is different for the central and border points of the facet. That is, the distance for the facet edge is longer by $\Delta S$. The change of polygon radius is given by:

$$\Delta R = D/2 (1/\cos(\beta/2) - 1) \tag{11}$$

Thus the increase of the scanning radius is given by:

$$\Delta S = 2\Delta R \cos\gamma = D \cos\gamma (1/\cos(\beta/2) - 1) \tag{12}$$

The sag of the focal surface is twice the depth of focus (DOF):

$$2DOF = S(1 - \cos\beta) - \Delta S \cos\beta \tag{13}$$

Thus the change of distance along the beam, which should be within the allowable defocus, is given by:

$$2DOF/\cos\beta = S(1/\cos\beta - 1) - D \cos\gamma (1/\cos(\beta/2) - 1) \tag{14}$$

Figure 14D:
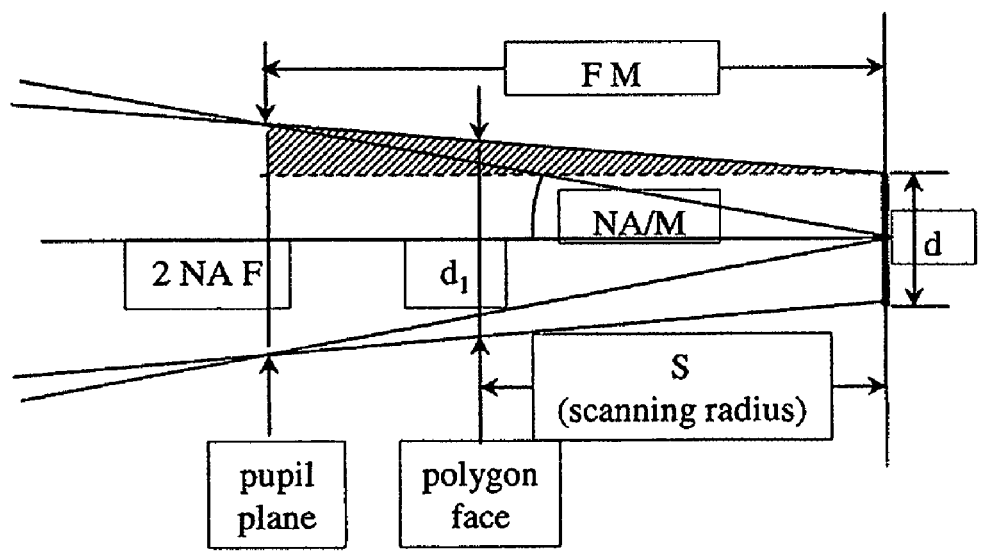

FIG. 14d is a detailed fragment of FIG. 14a. This is used to determine the required focal length (F) of the scanner. From similarity of the shaded triangles:

$$\frac{(d_1 - d)/2}{F \times NA - d/2} = \frac{S}{F \times M} \tag{15}$$

Evaluating F:

$$F = \frac{S \times d}{2S \times NA - M(d_1 - d)} \tag{16}$$

The rotational speed of polygon (v) is determined by linear scanning speed of spot V derived from equation (5):

$$v = V/(4\pi S) \tag{17}$$

Figure 15:
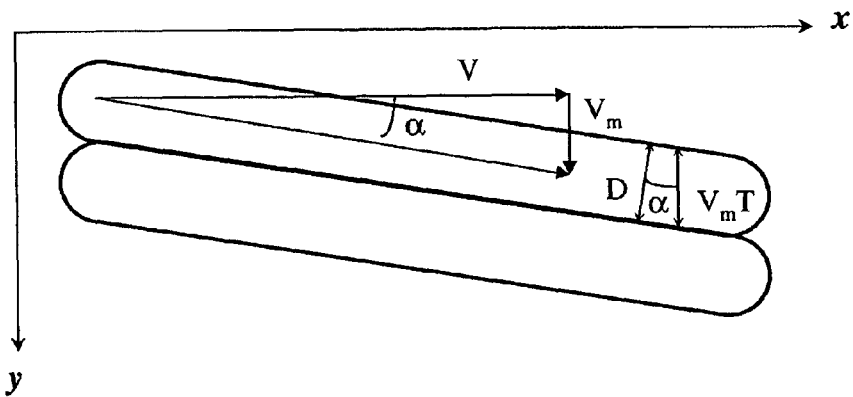
FIG. 15 is a diagram which depicts an area treated by a combination of scanning and manual movement of an embodiment of the device of the invention.
Figure 17:
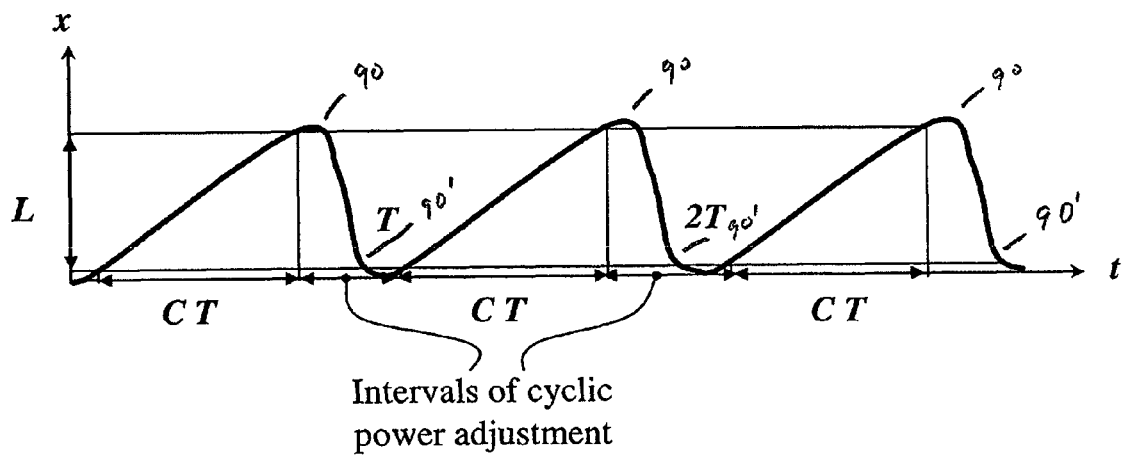

With each of the scanning embodiments described above, a strip of treated area at a desired depth is produced during each scan duration. The width of strip at the surface is equal to the spot diameter but increases with depth. As necessary, the same area may be treated over multiple passes to produce the desired degree of hair damage to modulate growth. The optimal manual speed should provide the shift of the strip by its width during the scan period. The scanning speed (V) is directed along the output window of the scanning head. The manual speed ($V_m$) is perpendicular to (V). From FIG. 15, it is seen that the scanning line is tilted to the direction of output window at angle determined by equation:

$$\tan\alpha = V_m/V \tag{18}$$

When the manual speed is optimal, the strip is shifted by its width (D) for the scanning period (T):

$$V_m^{opt} T \cos\alpha = D \tag{19}$$

Scanning length (L) can be expressed as:

$$L = VCT \tag{20}$$

where (C) is the useful fraction of scanning period, the duty cycle, of scanning. From the last three equations ($V_m$) is derived as:

$$V_m^{opt} = \frac{V}{\sqrt{\left(\frac{L}{CD}\right)^2 - 1}} \tag{21}$$

Substituting (V) from equation (5) into the last equation, the formula for the optimal amount of manual scanning speed is determined by:

$$V_m^{opt} = \frac{\frac{Kd}{\tau}}{\sqrt{\left(\frac{L}{CKd}\right)^2 - 1}} \tag{22}$$

The actual manual speed provided by operator is measured with movement sensor incorporated into the scanning head. The preferred design of this sensor is made similar to optical mouse and contains an illumination source such as an LED or diode laser, a detector, and a processor with an embedded algorithm for the speed calculation. When actual manual speed is higher than optimal one, the treatment area will contain untreated strips. If the scanning speed is not changed, this situation cannot be corrected by power adjustment and should be avoided. In one embodiment the device notifies the operator that manual speed must be reduced by generating a visual, audible or tactile warning signal.

Figure 16:
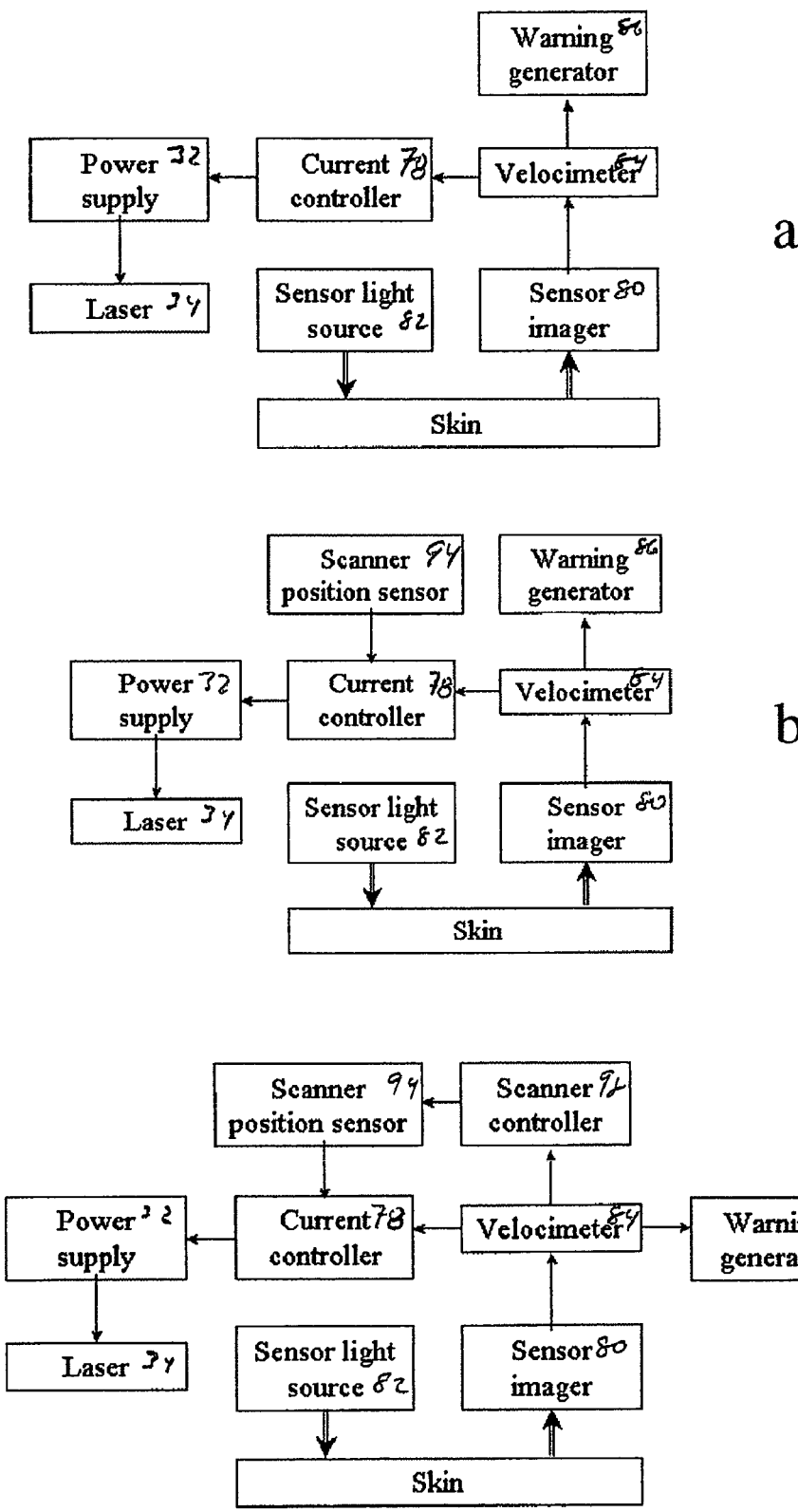
FIG. 16 (a-c) are block diagrams of various embodiments of a treatment device with velocity sensing and adjustment of laser power.

Referring to FIG. 16a, a block diagram of a system is shown that can detect the motion of the head across the skin. In each embodiment the power supply 32 generates the working current for the laser 34. The power to the laser 34 is controlled by a controller 78. The treatment device contains the movement sensor such as is used in an optical computer mouse. The small area of skin, which is not currently under the laser treatment, is illuminated by a light source 82. An image of this area is detected by image detector 80. Preferably, the spectral range of light source 82 and spectral sensitivity of image detector 80 should be different than the wavelength of the treatment laser 34. Otherwise, the image detected by 80 is distorted by the scattered and reflected light from laser 34. A light-emitting diode (LED) or low-power laser diode (LD) is used as a light source 82. The image detector 80 is made as a small two-dimensional CCD or CMOS array. The size of the array is large enough to generate the image pattern of skin, which is specific for each position of sensor. The period between sequential images is set to be smaller than the shortest time required for illuminated area to shift by its size over the skin.

A velocimeter 84 measures the speed of manual movement using a pattern recognition algorithm and the image frame period. It also compares the measured velocity with given amount of optimal manual speed. If the measured speed is higher than the optimal speed, the warning generator 86 is activated or the power/scan rate is adjusted. The warning generator 86 is implemented as a blinking LED and/or a beeper to let the operator know that manual speed should be reduced. If the measured speed is lower than the optimal one, the velocimeter 84 provides the ratio of the measured to the optimal speed to the controller 78. The controller 78 varies the power to provide the change of laser output power according to the equation (24) or (28) as shown below.

Figure 17:
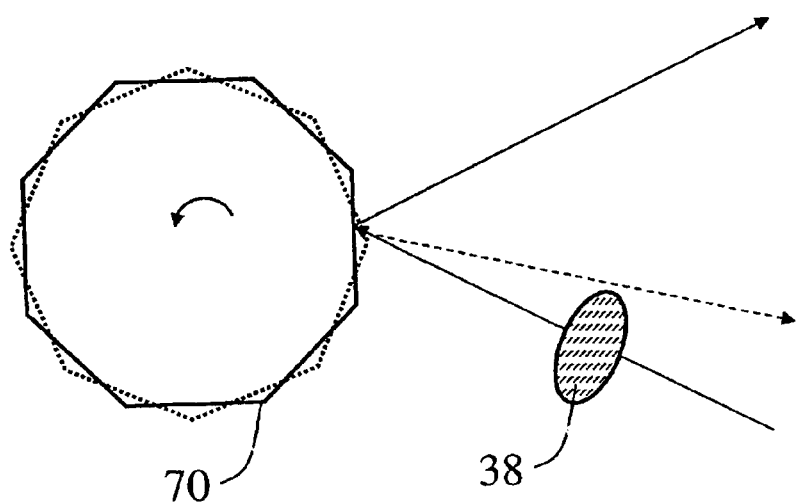
FIG. 17 is a graph showing the movement of the scanning spot with time as produced by the embodiments depicted in FIGS. 10, 12, 12a, 13.

For embodiments other than polygon-based one, additional power adjustment should be provided. In these cases, such as when the spot scanning achieved by an oscillating mirror movement as depicted in FIGS. 10 and 13. In these cases, the movement of the beam is shown generally in FIG. 17. The working range within the period (T) is limited by linear part of the curve when the spot displacement is uniformly increased with time. After the end of each working cycle, the spot is quickly returned to the initial position. This is necessary to provide for unidirectional beam scanning, which provides the continuous coverage of the treated area as shown in FIG. 17. The ratio of working range to the full period (T) gives the amount of duty cycle (C).

Near the turning points 90, 90' of the oscillation, the scanning speed of the spot is low. If the power delivered with spot is kept the same as during the fast phase of scanning, the skin at these points will be overheated. To avoid this, the power during the idle part of the period (1−C)T is reduced or can be turned off. This type of power adjustment will be called "cyclic," as opposed to the "corrective" adjustment described above. Cyclic power adjustment is not needed for the polygon-based scanning system because the spot speed is not varied in this case.

FIG. 16b shows the block diagram of the laser power adjustment for embodiments than polygon-based one. The current controller 78 is affected by signals from a scanner position sensor 94, in addition to those from velocimeter 84 as in FIG. 16a. Referring to the described above embodiments, the sensor measures the angular position of moving elements in designs of FIG. 10, or 13, or linear position of the fiber tip in design of FIG. 12. At the pre-determined positions, it gives the signals to controller for the reduction (or turning off) of the laser current and for its resuming.

In order to provide operator some range of manual speed, the movement with lower speed can be corrected by adjustment of laser power. In this case, each point of the treated area will receive multiple pulses of the same width. The number of pulses N is equal to the ratio between optimal and actual manual speed:

$$N = V_m^{opt}/V_m \quad (23)$$

The power should be adjusted so that the total target modification after delivery of N pulses is the same as from the single pulse. The power decrease depends upon whether the device is used to produce photochemical effects or thermal effects.

For photochemical reactions, such as production of active oxygen forms during photodynamic therapy (PDT), the number of transformed molecules is directly proportional to the number of absorbed photons. Therefore, the power should be adjusted in reverse proportion to the pulse number N. That is, the power should be adjusted, in direct proportion to the actual manual speed:

$$P = P_{opt} V_m / V_m^{opt} \quad (24)$$

The mechanism of photothermal reaction (selective photothermolysis) is more complicated. In this case, the light energy is used to heat the target and therefore accelerate the chemical reaction rate. As the target does not usually contain a light absorbing substance, the light first heats some distant object that contains high concentration of absorbing chromophore. The heat diffuses from the absorber to the surrounding tissues so the target temperature does not increase instantly with illumination but after the delay ($\tau_0$) called thermal relaxation time. The amount of ($\tau_0$) is proportional to the square of distance between absorber and target. The target selectivity is achieved by selection of light pulse duration ($\tau$) approximately equal to ($\tau_0$). If ($\tau < \tau_0$), the target temperature is not increased enough to accelerate the chemical reaction. At the terminal end of light pulse, only the regions that are closer to the absorber are heated. If ($\tau > \tau_0$), the heat diffuses too far from the absorber and may cause chemical modifications in surrounding tissues, not only in target. For the permanent hair removal, the hair shaft containing the highly absorptive chromophore, melanin, serves as an absorber, and hair bulb is considered target. The commonly used pulse width of 30 msec is roughly equal to the thermal relaxation time of hair bulb. In addition to the pulse width, the peak power should be also selected to provide enough target heating.

For thermally activated reactions, the reaction rate k is determined by Arrhenius law:

$$k = A \operatorname{Exp}(-\Delta E / RT) \quad (25)$$

where ($\Delta E$) is reaction activation energy, (A) is reaction rate at infinite temperature, and (RT) is thermal energy proportional to absolute temperature (T). Considering the number of transformed molecules the same for single and (N) pulses of the same duration, the connection between temperature ($T_1$) under optimal power and ($T_2$) under reduced power should be the following:

$$\operatorname{Exp}(-\Delta E/RT_1) = N\operatorname{Exp}(-\Delta E/RT_2) \quad (26)$$

The heating of the target is proportional to the laser power, because pulse duration is kept the same:

$$(T_1 - T_0)/(T_2 - T_0) = P_{opt}/P \quad (27)$$

Here $T_0 = 310K$ is human body temperature. From the last two equations, one can receive the equation for the power adjustment:

$$P = P_{opt} \frac{T_0}{T_1 - T_0} \left[ \frac{\frac{T_1}{T_0}}{1 - \frac{RT_1}{\Delta E} \ln\left(\frac{V_m}{V_m^{opt}}\right)} - 1 \right] \quad (28)$$

Adjusted power in equation (28) depends logarithmically on $V_m$, which is not as strong as the dependence on $V_m$ as given by equation (24). Therefore, only minor power adjustment is expected for thermally activated reactions.

Figure 18:
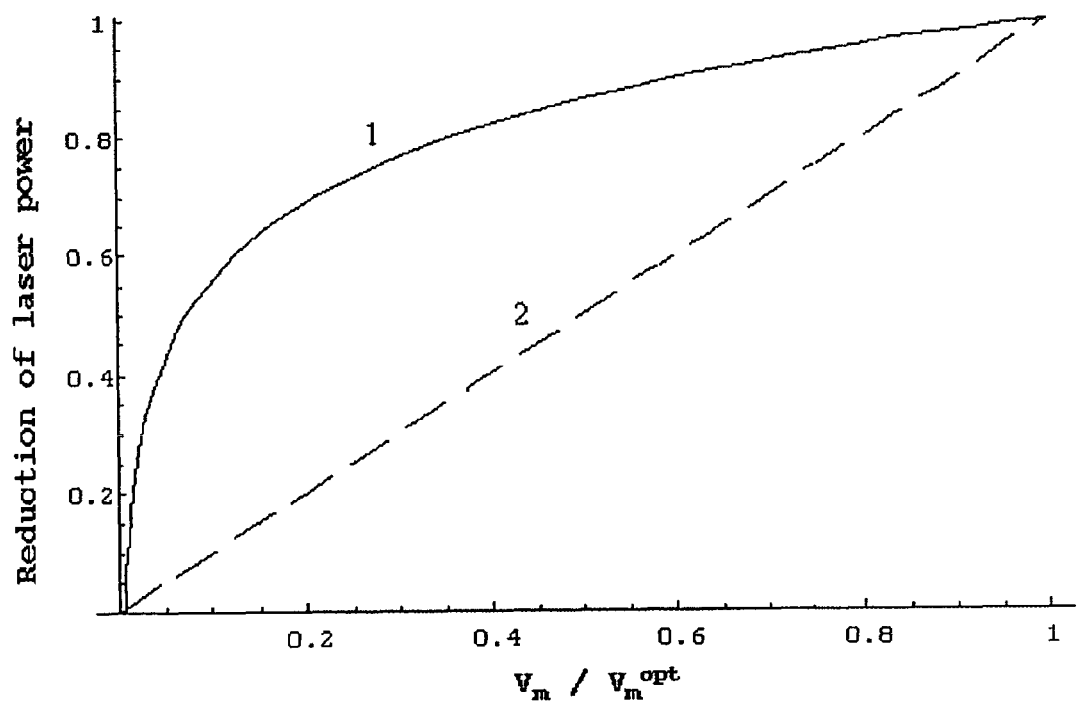
FIG. 18 is a graph of the reduction in laser power possible as the speed of use differs from the optimal speed.

FIG. 18 shows the decrease in power that can be used when the speed deviates from the optimal speed. The graph 1 refers to photothermal reaction and is based on equation (28). The values of the equation parameters used are reported in the literature: $\Delta E$=327 kJ/mol for bulk skin damage, and $T_1$=50° C. as a threshold temperature for reduction of enzyme activity. The graph 2 corresponds to photochemical reactions, in accordance to equation (24).

Referring again to FIGS. 16a, 16b, the current controller 78 provides the corrective power adjustment according to the equations (24) or (28) based on the signals from velocimeter 84. The set of input parameters: $V_m^{opt}$, selection between equations (24) and (28), $\Delta E$, and $T_1$ can be entered by the operator using a key digit pad separately or can be switched between the sets, which are generated for different tasks and saved in the device memory.

A more advanced way of corrective power adjustment can be achieved with simultaneous adjustment of scanning speed. Referring to equation (21) and FIG. 15, when scanning speed V varies in direct proportion to changing $V_m$ the treatment strips do not overlap each other and optimal treatment conditions are kept. In this case, there are no multiple pulses received by target but pulse duration is changed in the reversed proportion to the scanning speed. Under this condition, the photothermolysis produces the same amount of transformed molecules if the total delivered fluence is kept approximately constant. That means the power adjustment with simultaneous correction of scanning speed is described by equation (24) for both photothermal and photochemical reactions. But adjustment range for photothermolysis is limited at both extremes. Too low manual and scanning speeds should be avoided because the amount of pulse width ($\tau$) (see equation (5)) may become much more than thermal relaxation time ($\tau_0$) that is far from optimal conditions. Too high a manual speed would require according to equation (24) the output power higher than maximal value provided by the used laser. The operator is warned about using an out-of-range manual speed to avoid these conditions.

FIG. 16c shows the block diagram of the device with adjustment of both laser power and scanning speed. Velocimeter 84 affects current controller 78 in two ways. The first is the same as in FIG. 16a and 16b: the current is corrected to provide the satisfaction of equation (24) based on the data about the measured manual speed. In addition to corrective adjustment, the velocimeter 84 affects cyclic adjustment through a scanner controller 98, which varies the scanning speed in direct proportion to the manual one, and scanner position sensor 94. Again, the warning generator 86 is activated when manual speed is either too low or too high.

Occasionally the operator will manually pass the same area multiple times. This will not result in any problem with overdosing the treatment area but at the same time, there will be no added advantage compared to a single pass. The treatment effect from multiple pulses is considered above and described by equation (25), where the ratio $V_m^{opt}/V_m$ should be replaced with number of passes (N). One can see from FIG. 18 (curve 1) that the laser power can be kept almost the same until $N<10 (V_m/V_m^{opt}>0.1)$.

As multiple passes do not bring significant advantages but extend the treatment time, they preferably should be avoided. To provide this, some clearly visible substance can be applied to the part of the skin surface to be treated. Such substance can be for example foam similar to shaving cream, or colorized indicator liquid. The mentioned substance should not strongly absorb the treatment light. In this case, the scanning head is equipped with the surface cleaning means such as a plate with a blunt edge positioned perpendicular to the skin surface in front of output window. The length of this plate is equal to the length of the scanning line of the laser spot. During the manual movement of the scanning head, the cleaning means removes the covering substance from the treated part of the skin surface allowing operator to distinguish the treated from untreated parts. In one embodiment, the cleaning means does not remove the covering substance completely, but leaves a thin film on the surface. The residual film serves as a lubricant for the manual movement of scanning head on skin.

Although the specific embodiments described above are based on lasers, the non-coherent intense pulse light (IPL) sources can be used within the invention. The short pulse of IPL is typically provided by the discharge of a condenser battery having high capacitance. The battery is charged between pulses. The generated light is spectrally filtered in the desired wavelength range, and focused with reflective and refractive optics on the output window within a small spot. The following behavior of IPL light inside the skin does not differ from the diffusion of laser light, and can be used in all described embodiments. The only difference is the stepwise scanning manner of IPL spot because of pulse mode.

Although the invention has been described in terms of hair removal, the device can be used to treat other dermatological problems. Scanned small spot lasers that penetrate up to 3 mm into the skin have the potential to improve a variety of skin conditions such as vascular lesions, pigmented lesions and a variety of other conditions including photoaged skin and wrinkling. In the treatment of vascular lesions, absorption in hemoglobin with conversion of light to heat energy damages the endothelial lining and causes damage to papillary dermal vessels. The result is an improvement in facial telangiectasia, diffuse facial redness, facial flushing, as well as in the treatment of spider veins of the face and legs. Port wine stains and hemangiomas also respond to treatment with these devices. As long as the scanned time of the continuous wave scan spot is on the order of microseconds to milliseconds, sufficient thermal injury will be achieved to obtain improvement in this group of vascular lesions.

Pigmented lesions also respond to the scanned small spot devices. Lentigines, sun induced epidermal pigmented lesions and other epidermal pigmented lesions that are present at birth or delayed birth marks such as café au lait macules, Becker's nevus, nevus spillus also respond. Melasma and post-inflammatory hyperpigmentation, which are either combined epidermal and dermal pigmented disorders or solely dermal pigmented disorders, also respond to treatment by interrupting the dermal pigmentary process.

Photoaging presents as coarseness, roughness and sallowness of skin of skin as well as other changes including telangiectasia, dyspigmentation. All can be improved with the scanned small spot laser and light sources. Research has proven that a variety of different wavelengths from the short visible to the mid-infrared range stimulate new collagen production in the papillary and mid-dermis. The absorbing chromophore that initiates this change has not yet been determined. It appears, however, that a variety of different skin chromophores, including water, melanin pigment, and hemoglobin all can serve as the chromophore that absorbs the light to initiate this effect. Light energy converts to heat energy and by some yet to be determined biologic and cellular event, stimulates fibroblasts to produce new collagen. Studies have shown that a variety of these wavelengths can induce production of new type I and type III collagen fibers. Scanned small spot lasers and light sources also stimulate fibroblasts to produce collagen and induce, in effect, frequently terms "photorejuvenation." This change which is hardest to show photographically is easy to measure using profilometric measurement and also on skin biopsy. These biopsies show a Grenz zone of new collagen in the papillary dermis replacing the photo damaged collagen, and this accounts for the improvement in coarseness of skin, roughness of skin, skin texture. Absorption of light in vasculature and in pigmented areas accounts for the improvement of skin color, both red and brown, and for the total photorejuvenation effect.

Although the invention has been described in terms of using light as the energy source, it is anticipated that the energy source could also include microwaves, ultrasound and other directed sources when used with the proper system to provide narrow beam energy to the desired treatment depth without damaging tissues not meant for treatment.

The mechanism of microwave influence is based on the induction of electrical current in media, which is finally converted into heat. Therefore, the previous consideration about thermally activated chemical reactions can be applied to this case.

Ultrasound is often employed for its tissue heating functionality. However, the phenomena of resonant absorption, such as used in ultrasound lithotripsy applications, can also be integrated in the embodiments disclosed herein. If an object, such as a kidney stone, has a size that approaches the ultrasound wavelength, energy absorption can be strong enough such that the object is destroyed by resonant waves. To produce the desirable resonance, the object should respond to ultrasound, while the surrounding media, i.e. tissue, should remain unresponsive and undamaged. As the chemical structure and mechanical properties of hair are quite different from surrounding soft tissues of the body, it is reasonable to expect the resonant interaction between hair shaft and ultrasound to allow hair removal without tissue damage. Because of the resonant nature of the interaction, this embodiment requires less power than other direct thermal applications.

The embodiments described above are exemplary and the inventors intend only to be limited by the scope of the claims.

What is claimed is:

1. An apparatus for the treatment of skin comprising:
   (a) a source of energy for generating a spot of energy from the source impinging on the skin to provide a desired amount of energy to a desired depth for treatment;
   (b) a window having a replaceable contact device; and
   (c) a photosensitive indicator disposed about the contact device such that after a predetermined amount of energy is absorbed by the photosensitive indicator, the visible characteristics of the photosensitive indicator are modified to be an indicator to an operator that the contact device should be replaced.

2. The apparatus of claim 1 wherein the source of energy is selected from the group comprising lasers, laser diodes and flash lamps.

3. The apparatus of claim 1 further comprising an interlock in communication with the source of energy, to prevent energy from the source from exiting the apparatus unless apparatus is positioned to irradiate only the skin.

4. The apparatus of claim 3 wherein the interlock comprises a skin contact portion.

5. The apparatus of claim 1 further comprising a surface traversing means in communication with a housing surrounding a portion of the source, the surface traversing means adapted for indicating traversal of specific surface portions.

6. The apparatus of claim 5 wherein the surface traversing apparatus is a plate having an edge positioned adjacent to an output window in optical communication with the source.

7. The apparatus of claim 6 wherein the edge is sized to substantially equal a scan line length projected from the source.

* * * * *